US005679807A

United States Patent [19]
Murray et al.

[11] Patent Number: 5,679,807
[45] Date of Patent: Oct. 21, 1997

[54] PREPARATION OF TAXOL AND DOCETAXEL THROUGH PRIMARY AMINES

[75] Inventors: Christopher K. Murray, Longmont; Qun Y. Zheng, Superior; Xiaoqin Cheng, Broomfield; S. Kent Peterson, Denver, all of Colo.

[73] Assignee: Hauser, Inc., Boulder, Colo.

[21] Appl. No.: 380,679

[22] Filed: Jan. 30, 1995

[51] Int. Cl.$^6$ .................................................. C07D 305/14
[52] U.S. Cl. ........................................ 549/510; 549/511
[58] Field of Search ................................ 549/510, 511

[56] References Cited

U.S. PATENT DOCUMENTS

| | | | |
|---|---|---|---|
| 4,857,653 | 8/1989 | Colin et al. | 549/511 |
| 4,876,399 | 10/1989 | Holton et al. | 568/817 |
| 5,015,744 | 5/1991 | Holton | 549/510 |
| 5,319,112 | 6/1994 | Kingston et al. | 549/510 |
| 5,356,928 | 10/1994 | Murray et al. | 514/449 |

FOREIGN PATENT DOCUMENTS

| | | | |
|---|---|---|---|
| WO 92/09589 | 6/1992 | WIPO | C07D 305/14 |
| WO 94/07877 | 4/1994 | WIPO | C07D 305/14 |

OTHER PUBLICATIONS

Jitrangsri, Chote, "Approaches to the Synthesis of Modified Taxols," Dissertation submitted to the Faculty of the Virginia Polytechnic Institute and State University, UMI Dissertation Services (Aug., 1986).

D.G.I. Kingston, et al., "The Taxane Diterpenoids," *Progress in the Chemistry of Organic Natural Products* 61, pp. 1–206 (1993).

Gunda L. Georg, et al., "Schotten–Baumann Acylation of N–Debenzoyltaxol; An Efficient Route to N–Acyl Taxol Analogues and Their Biological Evaluation," *Bioorganic & Medicinal Chemistry Letters*, 4(2):335–338 (1994).

Debjani Dasgupta, et al., "Synthesis of a Photoaffinity Taxol Analogue and Its Use in Labeling Tubulin," *J. Med. Chem.*, 37:2976–2980 (1994).

Lalith Jayasinghe, et al., "Structure–Activity Studies of Antitumor Taxanes: Synthesis of Novel C–13 Side Chain Homologated Taxol and Taxotere Analogs," *J. Med. Chem.*, 37:2981–2984 (1994).

Charles S. Swindell, et al., "Characterization of Two Taxol Photoaffinity Analogues Bearing Azide and Benzophenone–Related Photoreactive Substiuents in the A–Ring Side Chain," *J. Med. Chem.*, 37:1446–1449 (1994).

David J. A. Schedler, et al., "Reductive Deoxygenation by $Cp_2ZrHCl$: Selective Formation of Imines Via Zirconation/Hydrozirconation of Amides," *Tetrahedron Letters*, 34(32):5035–5038 (1993).

Alexander G. Godfrey, et al., "Reductive Deoxygenation Using Hydridozirconium Enolates: A New Synthesis of $\alpha,\beta$–Unsaturated Esters," *Tetrahedron Letters*, 33(49):7461–7464 (1992).

L. Mangatal, et al., "Application of the Vicinal Oxyamination Reaction with Asymmetric Induction to the Hemisynthesis of Taxol and Analogues," *Tetrahedron*, 45(13):4177–4190 (1989).

*Primary Examiner*—Ba K. Trinh
*Attorney, Agent, or Firm*—Barbara A. Gyure

[57] ABSTRACT

The invention relates to a process for converting Taxol A, B and C to Taxol primary amine which can then be easily and efficiently converted to Taxol A or docetaxel, thereby significantly increasing the yield of these products from biomass. The method includes the removal of the amide from the side-chain with Schwartz's reagent to form an imine, followed by the hydrolysis of the imine to the primary amine. The primary amine can then be converted to Taxol A or docetaxel. New Taxol imine compounds and primary amine salts have been formed by this process.

27 Claims, 10 Drawing Sheets paclitaxel A    $R_1 = C_6H_5CO$ paclitaxel B, cephalomannine    $R_1 = CH_3CH=CCO$
                                              $|$
                                              $CH_3$ paclitaxel C,    $R_1 = n\text{-}C_5H_{11}CO$ primary amine (PA),    $R_1 = H$ $R_1$ = alkyl, aryl, vinyl, carbonyl or ether group
$R_2$ = H, alkyl, aryl, vinyl, ester, ether, or protecting group
$R_3$ = H alkyl, aryl, vinyl, ether, ester, glycoside, oxo-, or protecting group
$R_4$ = H or protecting group R₁ = alkyl, aryl, vinyl, carbonyl or ether group
R₂ = H, alkyl, aryl, vinyl, ester, ether, or protecting group
R₃ = H alkyl, aryl, vinyl, ether, ester, glycoside, oxo-, or protecting group
R₄ = H or protecting group R₂ = H, alkyl, aryl, vinyl, ester, ether, or protecting group
R₃ = H alkyl, aryl, vinyl, ether, ester, glycoside, oxo-, or protecting group
R₄ = H or protecting group
X = halogen or deprotonated organic acid R₁ = alkyl, aryl, vinyl, carbonyl or ether group
R₂ = H, alkyl, aryl, vinyl, ester, ether, or protecting group
R₃ = H alkyl, aryl, vinyl, ether, ester, glycoside, oxo-, or protecting group
R₄ = H or protecting group

PREPARATION OF TAXOL AND DOCETAXEL THROUGH PRIMARY AMINES

Our invention relates to a novel process for preparing the primary amine of Taxol, docetaxel and related compounds. Imines of Taxol, formed as intermediates in this process, and salts formed from the primary amine are also new.

BACKGROUND OF THE INVENTION

This invention relates generally to the field of preparing Taxol (which is also sometimes referred to as "paclitaxel" and a pharmaceutical composition of which is known as "TAXOL®", a registered trademark of the Bristol-Myers Squibb Company, Princeton, New Jersey) and certain of its precursors and related compounds including docetaxel (which is frequently referred to as "TAXOTERE®," a trademark of Rhone-Poulenc Rorer, Vitry-sur-Seine, France). The process of this invention also produces new taxane intermediate compounds, particularly certain imines and primary amine salts of Taxol and its derivatives.

Taxol is illustrated in FIG. 1A. Unless otherwise specified herein, "Taxol" refers collectively to the A, B and C variants as shown in that drawing. The term "taxane" refers to any compound having the cyclic structure characteristic of Taxol. Docetaxel is illustrated in FIG. 1B.

Taxol, a material occurring in nature, and extracted from *Taxus brevifolia* (i.e., the Pacific yew tree) and other biomass has been identified as having significant tubulin binding (Schiff, P. B., et al., "Promotion of Microtubule Assembly in vitro by Taxol," *Nature*, 277:665–67 (February 1979)) and, when delivered to the cell, cytotoxicological activity which has been demonstrated through Phase III clinical trials. Taxol A has been approved for treatment of refractory ovarian cancer and refractory breast cancer by the U.S. Food and Drug Administration (the "FDA"). Taxol A is also being investigated for the treatment of other forms of cancer. Because its mechanism of action is significantly different from that of other known cytotoxic agents, the development of Taxol has provided a significant new addition to the arsenal for treating cancer. Docetaxel, which acts in a similar manner, has also been identified as having cytotoxic activity. Docetaxel has not been approved for sale by the FDA, but it is still being evaluated in Phase III clinical trials.

Taxol A has two primary deficiencies. First, it is not water soluble, thereby complicating its delivery in vivo for therapeutic purposes. It is highly desirable to develop water soluble analogs of Taxol that may have appropriate pharmaceutical activity. Second, the supply of Taxol has been limited.

Generally, Taxol has only been isolated on a large scale from the bark of *Taxus brevifolia*; unfortunately, the yield of Taxol is relatively low even by the most efficient processes. The actual and potential demand for Taxol A far exceeds the supply currently available by extraction from natural sources. (Kingston, "The Chemistry of Taxol", *Pharmac Ther.*, Vol. 52, pp. 1–34, 5–6 (1991) [herein "Kingston"]. See also, Kingston et al., "The Taxane Diterpenoids," 61 *Progress in the Chemistry of Organic Natural Products*, Springer-Verlag/Wien, New York (1993)). The process described herein could significantly increase the yield of Taxol A from these sources.

Taxol is a complex compound represented by the formula shown in FIG. 1. The reference numerals designate site positions in accordance with standard Taxol nomenclature.

Because of the physical and chemical complexity of the Taxol molecule, the synthesis of Taxol is extraordinarily difficult. "[I]t is . . . quite unlikely that a commercially feasible synthetic route to taxol will be developed before the end of this century." (Kingston at p. 24.) "Despite the progress made in [synthesizing Taxol], the final total synthesis of Taxol is, nevertheless, likely to be a multi-step, tedious, and costly process." (U.S. Pat. No. 5,015,744 at col. 1, lines 59, et seq.) The complexities of synthesizing Taxol are evident from a cursory reading of Swindell, C. S. "Taxane diterpene synthesis strategies: A review." *Org. Prep. Proced. Int.* 23:465–543, 537 (1991) ("Swindell"). Although some announcements have been recently made by others regarding the synthesis of Taxol, the procedures employed appear, indeed, to be quite complex and unsuitable for commercial use.

Even the partial synthesis of Taxol from related compounds is quite difficult. "Taxol is the most functionally and stereochemically complex of the taxanes." (Swindell, at 467.) Among other things, the Taxol molecule presents numerous reaction sites with similar chemical constituents in close proximity. This presents a problem, for example, with respect to any reaction attempting to affect any of the numerous oxygen substituents present at positions 1, 2, 4, 5, 7, 9 and 10 of the taxane ring. (See, e.g., U.S. Pat. No. 4,876,399 to Holton et al., col. 3, lines 13–18.) This chemical complexity makes it difficult to direct reactions with significant specificity, except through the use of blocking agents or "protecting groups," and very controlled reaction parameters which favor a particular reaction at a particular site.

In addition, the stereochemistry of the Taxol molecule is considerably more complex than even the two dimensional formula depicted in FIG. 1. In fact, the Taxol molecule has been characterized as "an inverted cup shape, in which the ester side chain lies across the opening of the cup." (Kingston at 3.) Kingston includes a more detailed two-dimensional depiction of Taxol's stereochemistry.

As a result of these considerations, the chemistry of Taxol and Taxol related compounds has been difficult and unpredictable.

Taxol A is distinguished from several other variants, known as the "B" (sometimes called "cephalomanine") and "C" forms by the 3' amide group on the C-13 side chain attached to the taxane ring. The various structures for Taxol A, B and C are shown in FIG. 1. It is currently believed that other amide groups may also exist at the 3' site on taxanes occurring in natural biomass. Although Taxol B and C, as well as other amide compounds, are also present in biomass, to date only Taxol A has been approved for commercial use by the FDA. Accordingly, Taxol A must be separated or isolated from these other naturally occurring Taxol compounds in the preparation of commercial, therapeutic products. This separation can be difficult and expensive; the yield is quite low.

Although Taxol A, B and C differ only in the 3' amide group, prior to the invention set forth herein, there has been no known way to directly alter the amide group of these other Taxol compounds to form Taxol A. The primary reason for this is that the amide bond at the 3' site is much stronger than other bonds in the Taxol structure. Chemical reactions, such as hydrolysis, that might alter the amide are likely to attack preferentially these other sites, even when protected, causing cleavage and disassociation of the Taxol molecule. Accordingly, selective cleavage of the amide group in the presence of other labile groups in the taxane molecule is extremely difficult. (See, for example, Jitrangsri, C. "Approaches to the Synthesis of Modified Taxols," Virginia Polytechnic Institute and State University (1986), now available from UMI Dissertation Services, P.O. Box 1764, Ann Arbor, Mich. 48106–1764.)

Theoretically, it is possible to reduce the amide even in the presence of an ester. However, the reduction product is a substituted amine which is not generally suitable for further conversion to the primary amine. Thus, this methodology has not been useful for the overall conversion of Taxol amides to Taxol A. In contrast, the primary amine of Taxol B and C is a highly desired intermediate, which can be prepared from both compounds in the same reaction using the process of the present invention. Unlike the multi-step processes for the conversion of other materials, such as 10-deacetyl baccatin to Taxol, the primary amine is readily and efficiently converted to Taxol A or docetaxel using known techniques.

As a result of these difficulties, those who have reportedly converted Taxol B and C to Taxol A have done so by removing the entire C-13 side-chain and substituting a chain with the appropriate A-type amide. This process involves a number of steps, is complex, and wastes substantial amounts of expensive material.

In contrast, we have now found a simple and effective process for the partial synthesis of Taxol A directly from Taxol B and C by chemical conversion of the amide group to the primary amine. The process is also useful in other aspects of Taxol chemistry including, for example, the manufacture of Taxol derivatives and the production of docetaxel.

SUMMARY OF THE INVENTION

We have now discovered a simple, efficient and surprisingly selective process for converting Taxol B and C to Taxol A. The method described herein includes reductive deoxygenation of the amide with Schwartz's reagent to form an imine, followed by conversion of the imine by hydrolysis to the primary amine. Indeed, where the starting material is not protected, a small amount of the Taxol will be converted directly to the primary amine by reaction with Schwartz's reagent. The primary amine, the structure of which is illustrated in FIG. 1, can then be converted to Taxol A, docetaxel or other Taxol derivatives.

As described more fully herein, the present invention has a number of objects and advantages. Among these are the fact that the present invention can increase significantly the amount of Taxol A or docetaxel which can be recovered from *Taxus brevifolia* or other biomass sources.

It is a further object of the present invention to produce certain novel Taxol immines and to produce Taxol primary amines both of which can be used as precursors for preparing Taxol A, docetaxel or other Taxol derivatives. Among these derivatives are novel primary amine salts which are water soluble.

In addition, it is an object of the present invention to provide a simple and efficient process for converting Taxol to docetaxel.

All of these objectives and others are achieved using chemical reactions that are mild, efficient and selective as described herein.

DETAILED DESCRIPTION OF THE INVENTION AND THE PREFERRED EMBODIMENT

We have now discovered a process for the conversion of Taxol A, B and C amide groups to the primary amine.

The conversion of the amide to the primary amine is effected utilizing an effective reductive deoxygenation amount of $Cp_2ZrHCl$ (i.e., zirconocene chloride hydride in which "Cp" is cyclopentadienyl; the compound also being known as "Schwartz's reagent"). Unlike other reducing agents unsuccessfully tried in the past, the controlled reduction of the Taxol amide groups using Schwartz's reagent results in imine, primary amine, and, possibly, aminal compounds that are readily converted into Taxol A or other Taxol-related compounds.

Figure 3:
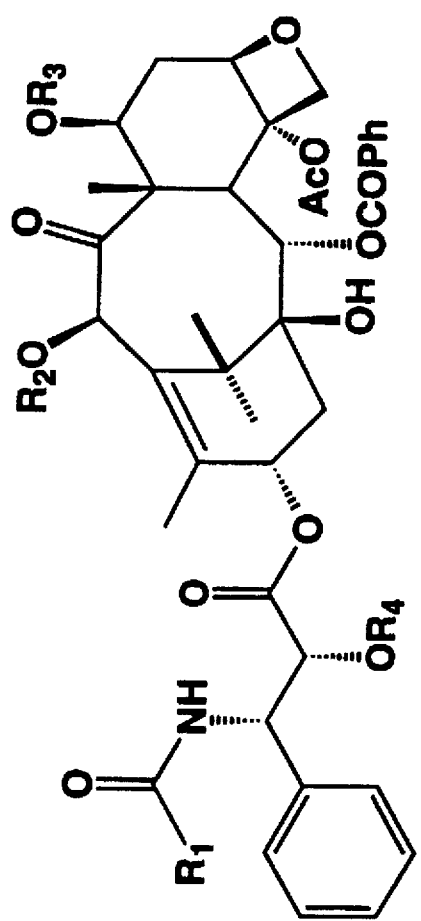
FIG. 3 illustrates known taxane-starting materials for use in the process of the present invention.

Appropriate starting materials for use in the current invention include any taxane having a C-13 side chain with a 3' amide group. Acceptable starting materials include those. shown on FIG. 3. In addition to the use of Taxol A, B and C as starting materials, the process can be employed with 10-deacetyl Taxol (i.e., "10-DAT") with the A, B and C amide structures. Further, the foregoing starting materials may include naturally occurring compounds having a xyloside at the C-7 position or the "oxo-" compound derived from oxidation of the xyloside as described in U.S. Pat. No. 5,356,928, issued Oct. 18, 1994, which is incorporated by reference herein. The starting materials may include compounds that are unprotected or those that have been protected at the C-7, C-10 and 2' positions using standard techniques, such as triethylsilylation, known to those skilled in the art.

Figure 4:
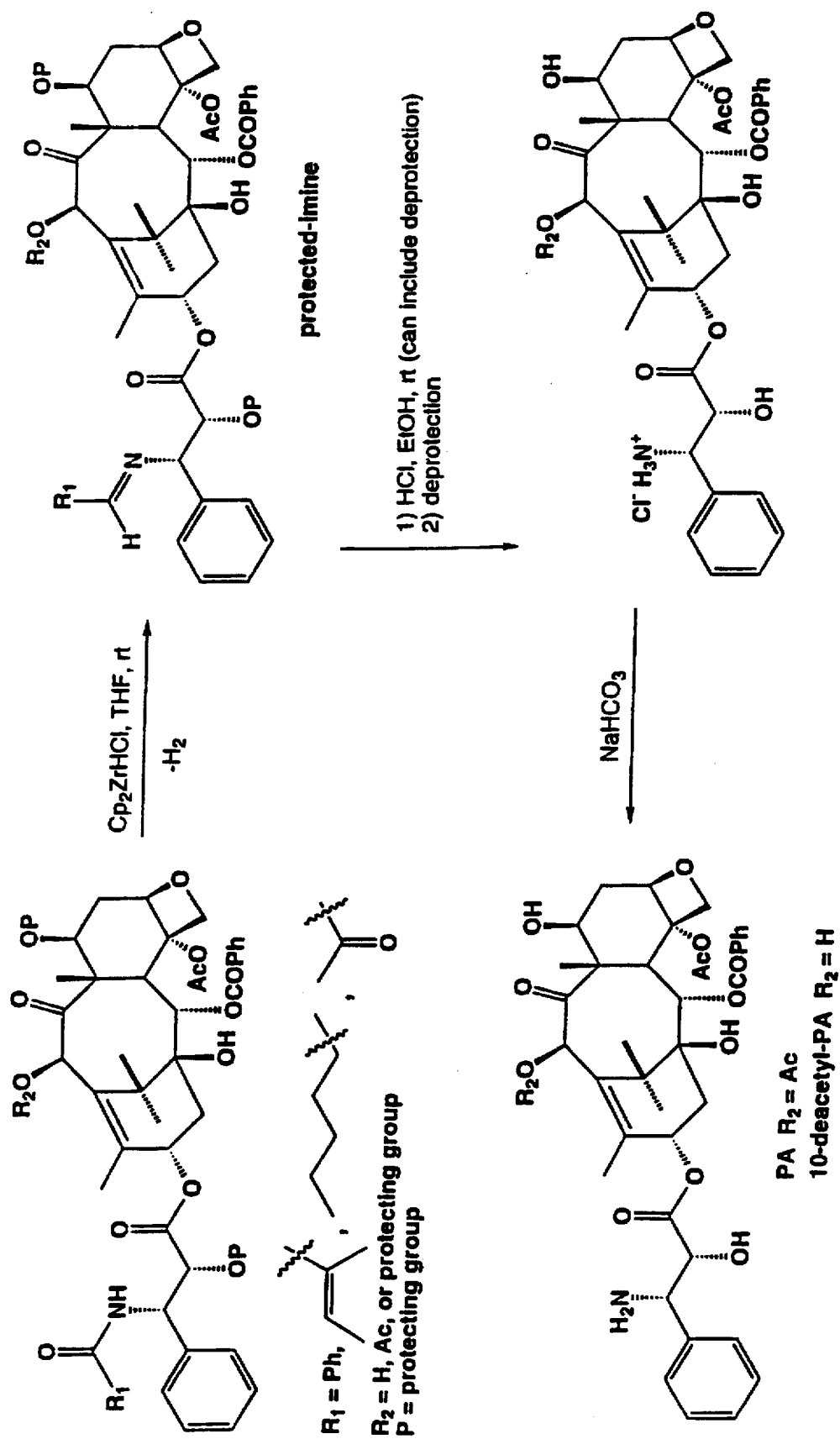
FIG. 4 is a schematic illustrating the formation the primary amine of Taxol utilizing the process of the present invention, with protection of other possible reaction sites on the starting material.

The process for conversion of protected starting materials is illustrated in FIG. 4. As depicted, the 7-, 10- and 2'-OH groups may all be protected using any standard technique, preferably triethylsilylation. Trimethylsilyl and trichloroethoxycarbonyl are examples of other protecting groups that are conventionally utilized in Taxol chemistry. Preferably, both the 7 and 2' groups are protected because these are the most reactive. At a minimum, the 2' group should be protected to provide maximum conversion. After appropriate sites are protected, the amide is reacted with Schwartz's reagent, resulting in the formation of the imine compounds. The imine compounds are then easily converted to the primary amine as shown on FIG. 4. The imines and the process of converting them to the primary amines are described more fully below.

Figure 5:
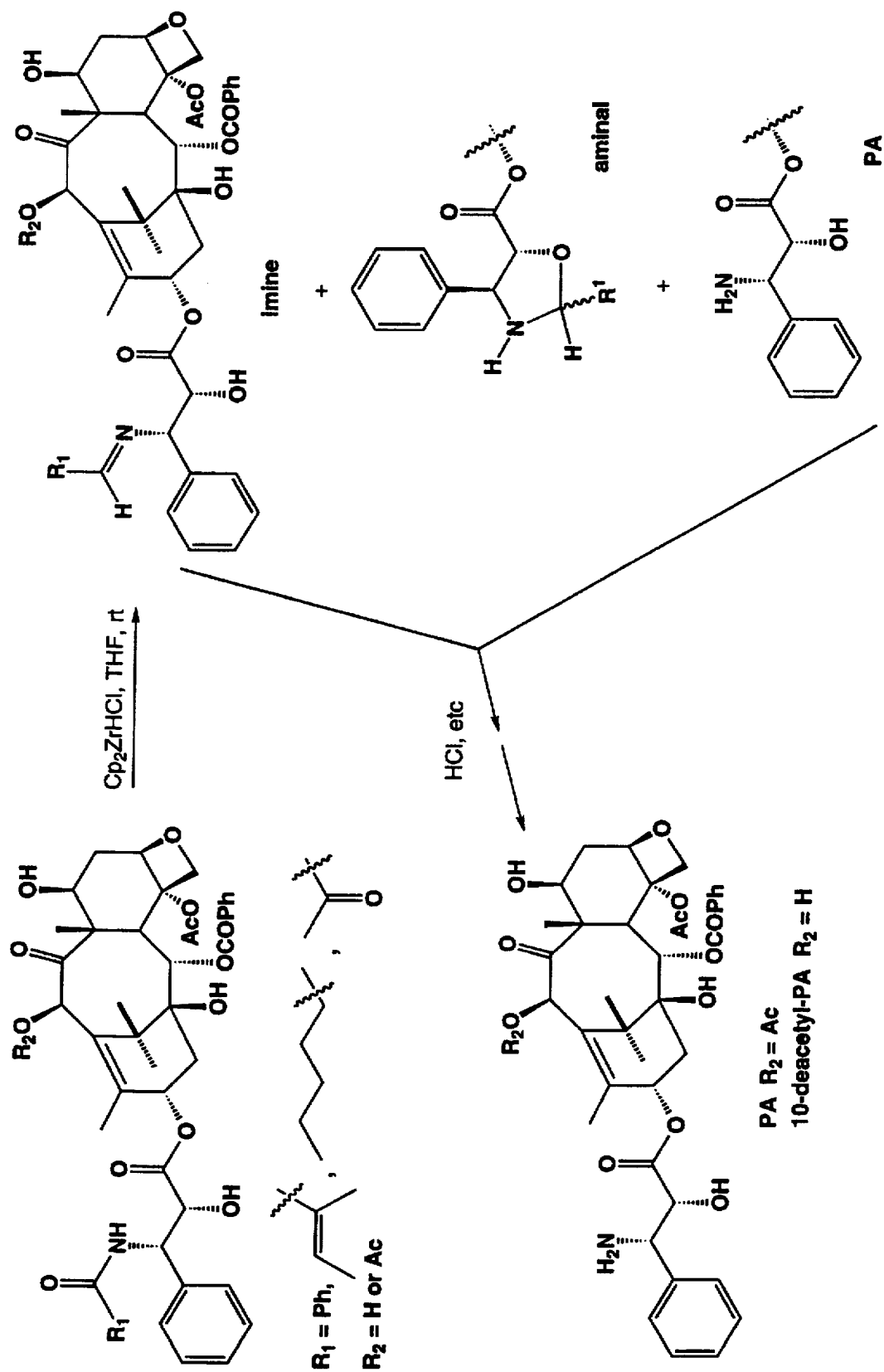
FIG. 5 is a schematic illustrating the formation of the primary amine of Taxol utilizing the process of the present invention, without protection of other possible reaction sites.
Figure 6:
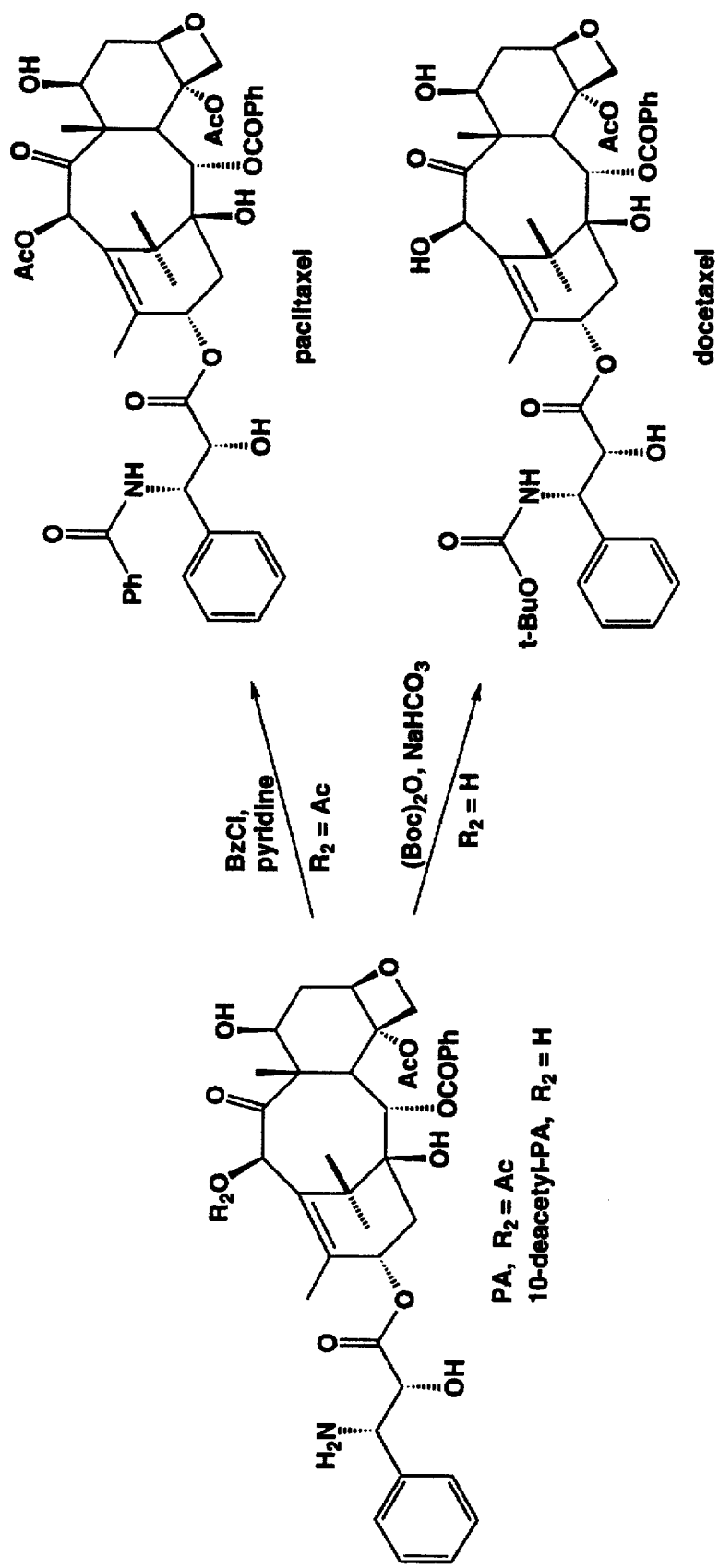
FIG. 6 is a schematic illustrating: (1) the conversion of the Taxol primary amine to Taxol; and (2) the conversion of the primary amine of 10-deacetyl Taxol ("10-DAT") to docetaxel.

FIG. 5 generally shows the process by which an unprotected Taxol starting material is converted with Schwartz's Reagent. In this case, the conversion results in an intermediate mixture of imine and primary amine compounds. The imines are then converted to the primary amine as shown. Although FIG. 5 might suggest that the primary amine is formed more easily, i.e., directly, from unprotected starting material, in fact, the amount of unprotected starting material directly converted to the primary amine by Schwartz's reagent is quite small. Accordingly, the preferred embodiment uses protection and deprotection of the starting material.

Various amounts of Schwartz's reagent can be employed, but generally the reagent should be present in the range of 1–10 molar equivalents per mole of amide. Preferably, at least 2 equivalents of Schwartz's reagent per mole of amide is needed for optimum yields of imine. Preferably, the reaction is conducted with tetrahydrofuran ("THF") as the solvent.

The amide is converted to the imine in 2 to 8 hours for solutions which are approximately 100 mg./ml. of taxane using 2–10 molar equivalents of Schwartz's reagent in THF. Preferably, Schwartz's reagent is added in the presence of an inert gas, such as, argon.

Figure 7:
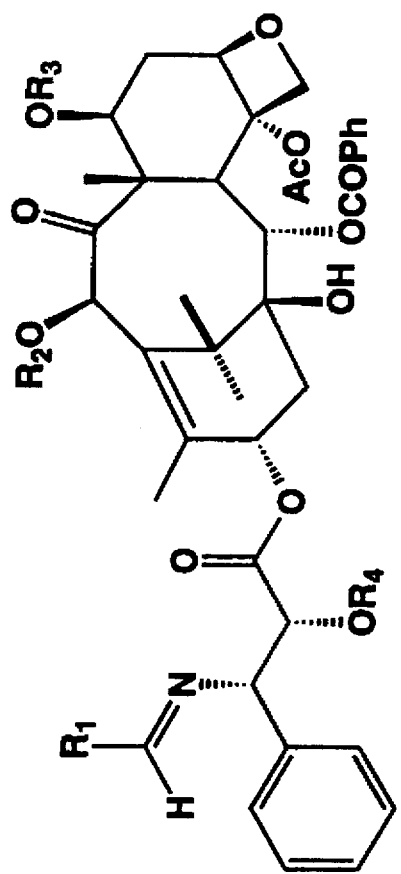
FIG. 7 is a general chemical structure for the novel Taxol imine compounds produced by the process described herein.

The treatment of the amide with Schwartz's reagent results in the formation of the imine and the release of hydrogen. The general formula for the imine compounds formed from known Taxol compounds commonly found in biomass is shown on FIG. 7. The exact material produced by reduction depends on which of the starting materials noted previously has been employed. Representative novel imine compounds have been separately isolated and their existence has been confirmed through the use of direct NMR and mass spectral analysis as illustrated in the examples. While the imines appear to be stable in the reaction mixture, isolation through the use of chromatography appears to cause some degradation.

Figure 9:
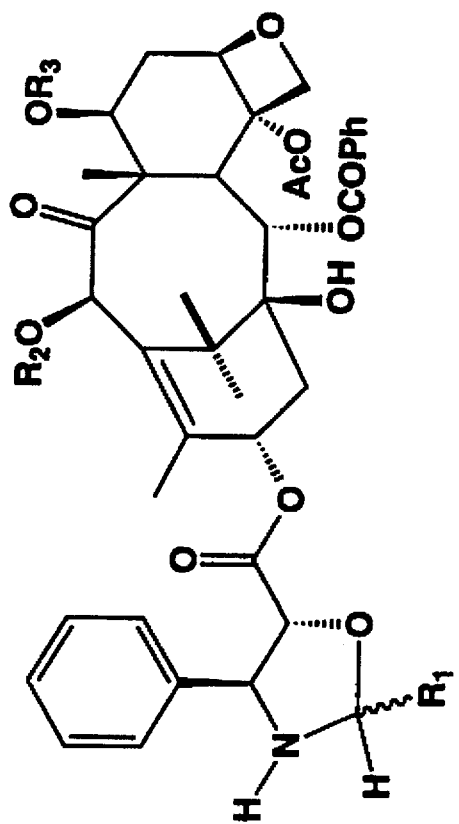
FIG. 9 is a general chemical structure for the novel aminal compounds produced by the process described herein.

We also believe that certain novel aminal compounds are formed as intermediates, at least temporarily. These compounds are illustrated in FIG. 9. The existence of these aminal compounds is consistent with mass spectral data, but has not been confirmed by NMR or other definitive techniques at the present time. Again, the exact material produced will depend on which of the starting materials noted previously has been employed.

The imines produced from the reaction with Schwartz's reagent can then be converted to the primary amine through acid hydrolysis followed by neutralization and extraction with organic solvent. As illustrated in FIG. 4 and in several of the examples herein, the hydrolysis can be accomplished using aqueous HCl in solution with protic solvent, such as ethanol. Other acids may be employed, such as aqueous HBr. Other suitable solvents include methanol, tetrahydrofuran, or dioxane. Theoretically, at least two moles of acid should be present per mole of imine. In addition to hydrolyzing the imine, the use of HCl may also remove triethylsilyl protecting groups. However, when other protecting groups and acids are used, it may be necessary to remove the protecting groups separately. When hydrolysis is complete, the solution should be neutralized with a base, such as $NaHCO_3$. The primary amine can then be extracted using an organic solvent, such as $CH_2Cl_2$ or aprotic solvent. Other work-up procedures might also be employed.

The primary amines can be converted to Taxol or docetaxel as shown schematically in FIG. 4. The processes for converting certain primary amines to Taxol or docetaxel have been demonstrated before. The primary amine can be further converted efficiently into Taxol A using known techniques. For example, the conversion can be effected using the process shown in Mangatal, L., et al. "Application of the Vicinyl Oxyamination Reaction with Asymmetric Induction to the Hemisynthesis of Taxol and Analogues," 45 *Tetrahedron No.* 13, pp. 4172–90 (1989). Preferably, the Taxol primary amine is dissolved in ethyl acetate and reacted with benzoyl chloride in the presence of sodium bicarbonate. Alternatively, the Taxol primary amine is dissolved in pyridine and reacted with benzoyl chloride; the product is washed in weak $CuSO_4$ solution. Similarly, the 10-deacetyl primary amine can be converted to docetaxel by dissolving in ethyl acetate and reacting with $NaHCO_3$ and di-tertiarybutyldicarbonate.

The reductive deoxygenation with Schwartz's reagent, imine hydrolysis and the subsequent conversion of the primary amine are mild, selective and efficient. These reactions are mild enough that their progress can be monitored, and they do not continue beyond the desired endpoint to produce unwanted products. Generally the reactions can be monitored utilizing high-pressure liquid chromatography ("HPLC") and thin-layer chromatography ("TLC"). When the presence of taxane starting material or imine intermediate is no longer detected, the reaction is deemed to be complete.

The reaction resulting in reductive deoxygenation of the amide and formation of the imine is quite selective. This is true in two respects. First, the reaction occurs selectively to reduce the amide on the 3' site. Normally, one should anticipate that the introduction of a reducing reagent to Taxol would cause reactions at sites other than the 3' site. The reactions can be carried out without protection of other sites, indicating the inherent selectivity of the process. On the other hand, the use of protecting groups at the C-10, C-7 and 2' sites is preferred, as previously discussed, and the yield is increased in that manner.

Secondly, the reactions can be carried out in mixtures containing Taxol A, B and C and other Taxol related compounds without impairing the results. Such mixtures occur in biomass or partial separations or extracts from biomass. Indeed, the process of the present invention provides a common means to convert a mixture of Taxol A, B and C to a single primary amine compound, all of which can be subsequently converted to Taxol A and separated or purified, in the proper order as the case requires. Thus, the amides may be converted to the primary amine at various stages during the isolation of Taxol from Taxus brevifolia or other naturally-occurring materials.

Finally, the conversion of the amide to the primary amine is relatively efficient. Although the process has not been maximized, it has been possible to obtain more than 50% conversion of the amides to the primary amine. The exact yield of Taxol or Taxol precursors depends on the amount of taxane starting material and the procedures employed in the isolation and purification of the reaction products. Significant improvements in yield above the 50% conversion level will undoubtedly be obtained as the process is further developed.

Prior to this invention, no viable process has existed for the conversion of Taxol B and C to Taxol A through transformation of the amide group. The conversion of the amide to the amine represents an opportunity to obtain much more Taxol or Taxol derivative from biomass via additional semi-synthesis than is currently available by isolation alone. The conversion may be conducted on a crude mixture of taxanes that are all converted to the primary amine so that the processing costs of isolation alone can be reduced. The make-up of the crude mixture of taxanes may be controlled by early purification steps on the biomass extract.

For example, biomass or a biomass extract containing Taxol A, B and C can be treated with Schwartz's reagent to produce the imine which is then converted to the primary amine. At this point, the primary amine can be purified from the modified biomass mixture by precipitation, crystallization or chromatography. The primary amine is then converted to Taxol A. As shown in Example 1, even Taxol A is processed in this manner through the imine and the primary amine back to Taxol A itself. This is in contrast to the rather difficult separation of Taxol A from the Taxol B and C forms contained in the original biomass utilizing current technology. Thus, the process of producing Taxol is greatly simplified and the yield of Taxol A is significantly increased.

Figure 1A:
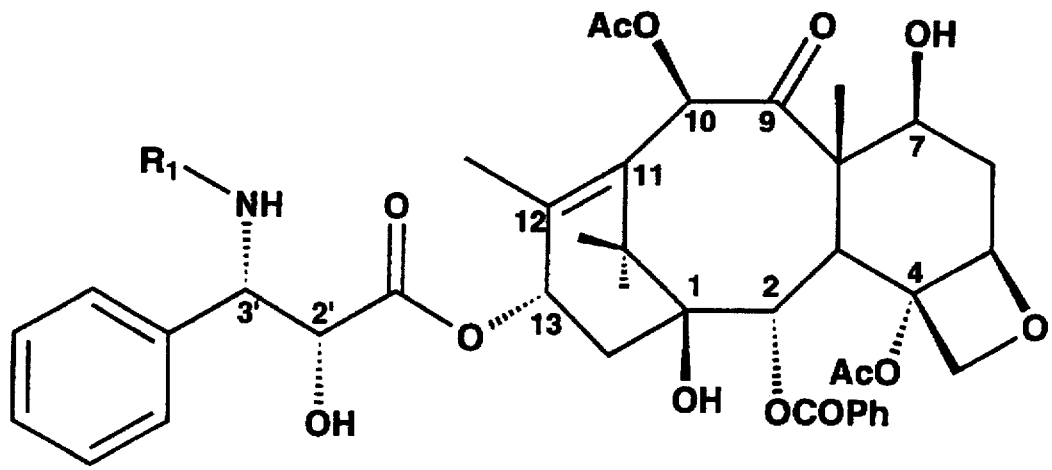
FIG. 1A shows the chemical structures for Taxol A, B and C. It also shows the structure of the primary amine, which can be formed from each of these Taxol forms using the process of the present invention.
Figure 1B:
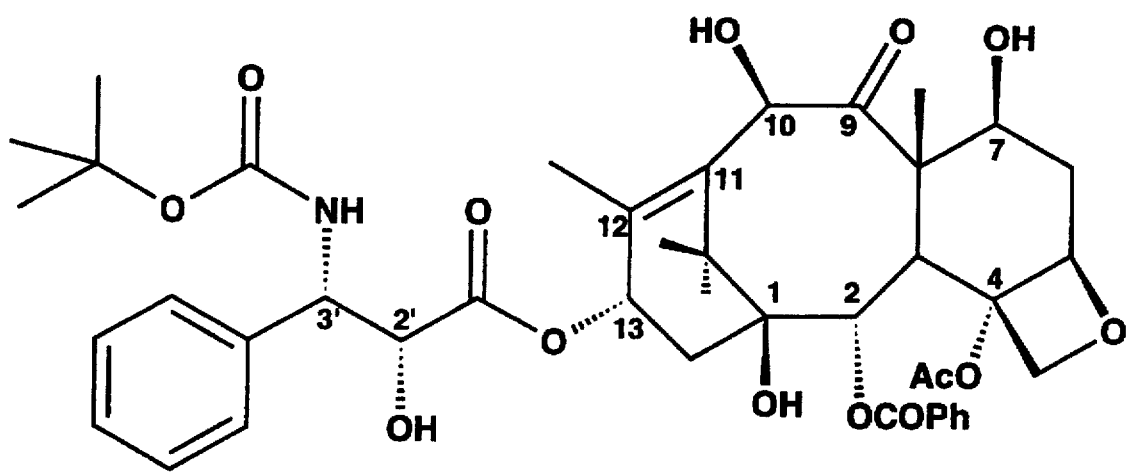
FIG. 1B shows the chemical structure for docetaxel.
Figure 2:
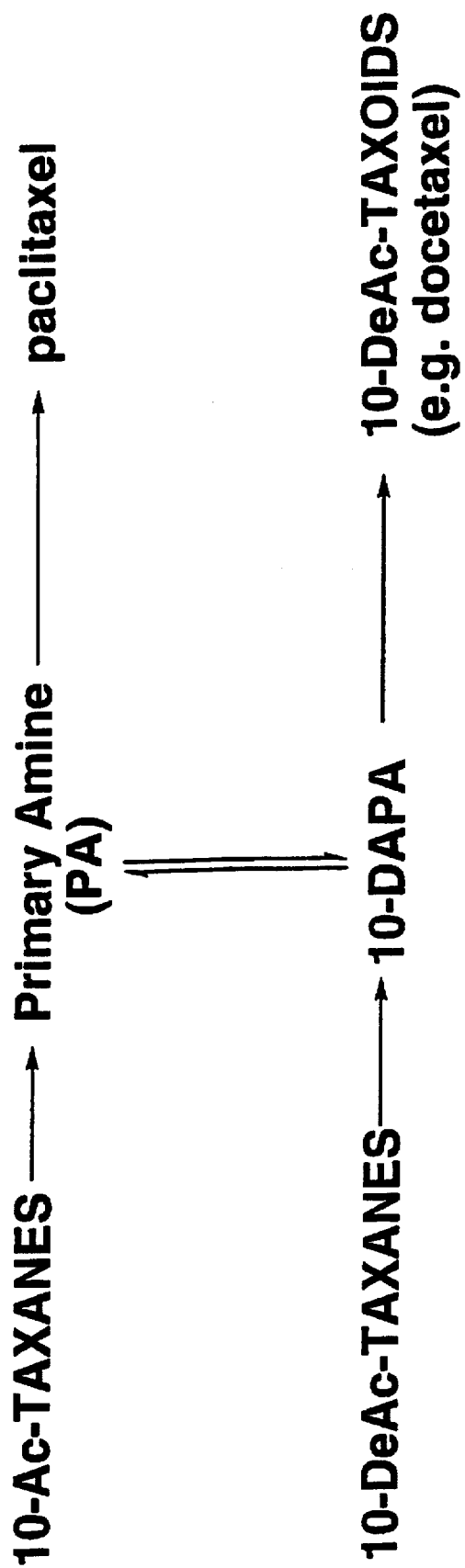
FIG. 2 is a schematic showing available options for preparing Taxol A or docetaxel from Taxol A, B and C or from the 10-deacetyl form of these same Taxol compounds.

As illustrated in FIG. 2, a significant advantage of the present invention is that it can be used as part of a scheme to further maximize the production of Taxol through acetylation of certain 10-deacetyl precursors or to maximize the production of docetaxel through deacetylation of Taxol A, B and C. For example, a mixture of biomass containing Taxol (A, B and/or C) and 10-deacetyl Taxol (A, B and/or C) can be converted to the primary amines followed by acetylation of the 10-deacetyl compounds and conversion to Taxol A. Alternatively, the same mixture can be converted to the primary amines followed by deacetylation of the C-10 site and conversion to docetaxel. The processes of acetylation and deacetylation are known to those skilled in the art. In addition, treatment of a THF solution of Taxol or other 10-acetylated taxane with hydrogen peroxide in the presence of a mild base, such as sodium bicarbonate, results in selective and efficient deacetylation at the 10-position. This process is illustrated in Example 27.

The step of acetylation or deacetylation, whichever is appropriate, and the step of conversion to the primary amine may be conducted in any order. Similarly, extraction of the material from the biomass may be conducted in various sequences relative to these reaction steps. In general, however, it is more efficient to convert the maximum amount of material to the desired end product before final extraction. Thus, a pool of derivatives may be converted as a group and then isolated. As illustrated on FIG. 2, through deacetylation or acetylation, the production of Taxol or docetaxel from biomass can be further maximized.

Figure 8:
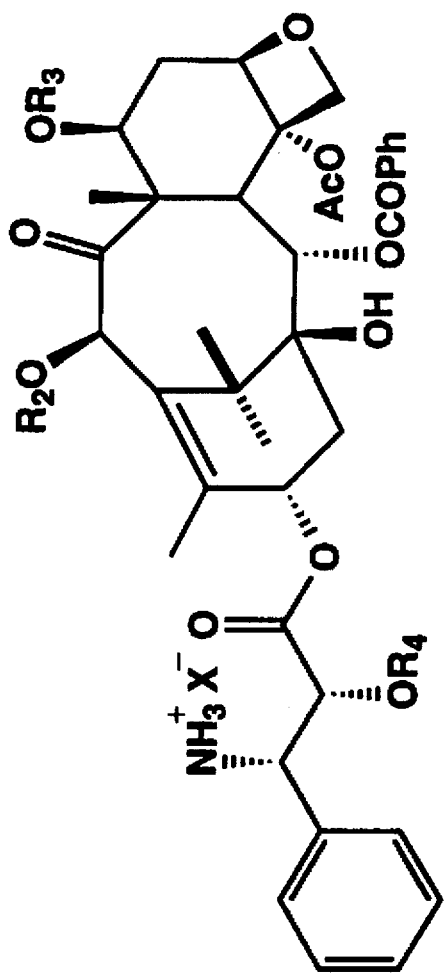
FIG. 8 is a general chemical structure for the novel Taxol primary amine salts also produced by the process described herein.

A further advantage of the present invention is that it can be used to prepare other, valuable Taxol derivatives. Because the Taxol primary amines are quite reactive, they are good platforms for the preparation of additional Taxol derivatives, not heretofore possible. For example, Taxol primary amine salts can be prepared from the primary amine in accordance with known techniques and are generally depicted in FIG. 8. These compounds are water soluble and are easily reacted in aqueous environments to form other derivatives. The salts or other water soluble derivatives may also be more easily delivered for in vivo therapeutic applications, should these compounds prove to have pharmacological activity.

The novel process and compounds of our invention are illustrated by the following examples:

EXAMPLES

Summary: For convenience, the following is a brief overview of the various examples.

Examples 1–3 demonstrate the conversion of Taxol A derivatives with triethylsilyl protecting groups on the 2' and 7 OH groups to the Taxol primary amine.

Examples 4–6 demonstrate the conversion of Taxol B(cephalomannine) derivatives with triethylsilyl protecting groups on the 2' and 7 groups to the primary amine.

Example 7 demonstrates the conversion of 2', 7-bis (triethylsilyl)oxidized Taxol B to 2',7-bis(triethylsilyl) oxidized Taxol B imine and further conversion to Taxol primary amine.

Examples 8 and 9 demonstrate the conversion of Taxol C derivatives with triethylsilyl protecting groups on the 2' and 7 groups to the Taxol primary amine.

Examples 10 and 11 demonstrate the conversion of 7-xylosyl Taxol derivatives with triethylsilyl protecting groups on the 2', 7, and xylosyl OH groups to the 7-xylosyl Taxol primary amine.

Examples 12 and 13 relate to the conversion of Taxol A derivatives with trimethylsilyl protecting groups on the 2' and 7 OH groups to the Taxol primary amine.

Example 14 demonstrates the conversion of Taxol A derivatives with trichloroethoxycarbonyl protecting groups on the 2' and 7 OH groups to the Taxol primary amine.

Examples 15 and 16 relate to the conversion of Taxol primary amine to Taxol.

Examples 17–19 demonstrate the conversion of 10-deacetyl Taxol A derivatives with triethylsilyl protecting groups on the 2' and 7 OH groups to the 10-deacetyl Taxol primary amine.

Examples 20 and 21 relate to the conversion of 10-deacetyl Taxol C derivatives with triethylsilyl protecting groups on the 2' and 7 OH groups to the 10-deacetyl Taxol primary amine.

Example 22 relates to the conversion of 10-deacetyl Taxol primary amine to docetaxel (i.e., "TAXOTERE").

Example 23 relates to the conversion of Taxol to Taxol primary amine without using protecting groups.

Examples 24 and 25 relate to the conversion of a mixture of Taxol A, Taxol B (cephalomannine), and Taxol C to Taxol primary amine.

Example 26 relates to the conversion of Taxol primary amine to Taxol primary amine hydrochloride salt.

Example 27 shows one preferred method for deacetylation of Taxol.

Materials and Methods: All solvents and reagents employed in the examples were used as received from the manufacturer. The taxanes were isolated from the bark of *Taxus brevifolia*. Reactions were monitored by thin-layer chromatography ("TLC") using 0.25 mm. Whatman Silica Gel 60A K6F (glass support) or 0.25 mm. E. M. Industries Silica Gel 60 (aluminum support) silica gel plates. Reactions were also monitored by high-pressure liquid chromatography ("HPLC") using a system consisting of a model L-6200 pump, Model AS-4000 or L-3000 UV/VIS/DAD detector (Hitachi Instruments, Inc.). The system was equipped with an NEC 286 computer with 40M hard drive and Lab Manager HPLC software (Hitachi Instruments, Inc.). HPLC columns used included a 4.6 mm.×250 mm. Phenyl column, packed with 5 μm diphenyl material (Supelco, Inc.); a 4.6 mm.×250 mm., 5 μm, 60 angstrom Pentafluorophenyl (PFP) column (ES Industries); and a 4.6 mm.×20 mm. phenyl guard column (Jones Chromatography). Silica Gel for flash chromatography (230 to 400 mesh) was supplied by Scientific Products. Yields refer to chromatographically and spectroscopically pure compounds unless otherwise noted. As used herein, "chrom purity" refers to the HPLC normalized peak area percentage at 227 nm for a given component.

Melting points are uncorrected. $^1$H-NMR and $^{13}$C-NMR chemical shifts are reported in ppm, relative to tetramethylsilane using residual non-deuterated NMR solvent for reference. NMR data was obtained using a JEOL Eclipse 400 MHz NMR spectrometer. Low resolution mass spectra were measured using a VG platform (API mass spectrometer)—electrospray mode. High resolution mass spectra were measured using a VG Analytical ZAB.

Example 1

This example demonstrates the conversion of 2',7-bis(triethylsilyl) Taxol to 2',7-bis(triethylsilyl) Taxol imine and 2',7-bis(triethylsilyl) Taxol primary amine.

A sample of 2',7-bis(triethylsilyl) Taxol (330.8 mg, 0.31 mmol) was dissolved in THF (3.1 mL). Zirconocene chloride hydride was added (236.7 mg, 0.92 mmol) and the reaction stirred at 25° C. under $N_2$. After 2 hours the reaction appeared complete by TLC analysis. The crude mixture was poured into cold hexanes, and the resulting precipitated Zr complexes were filtered off. The solvent was removed under reduced pressure, to give a white solid (326 mg). Silica gel chromatography (25% EtOAc/hexane) yielded 2',7-bis(triethylsilyl) Taxol imine (193.8 mg, 59%). $^1$H NMR (400 MHz, CDCl$_3$) δ0.49–0.61 (m, 12H), 0.86–0.93 (m, 18H), 1.10 (s, 3H), 1.15 (s, 3H), 1.64 (s, 3H), 1.68 (m, 1H), 1.85 (m, 2H), 1.90 (s, 3H), 2.15 (s, 3H), 2.32 (s, 3H), 2.49, (m, 1H), 3.67, (d, J=7.32 Hz, 1H), 4.12 (d, J=8.3 Hz, 1H), 4.26 (d, J=8.24 Hz, 1H), 4.42 (dd, J=6.7, 10.3 Hz, 1H), 4.50 (d, J=8.4 Hz, 1H), 4.55 (d, J=8.44 Hz, 1H), 4.90 (d, J=8.04 Hz, 1H), 5.57 (d, J=6.96 Hz, 1H), 5.90 (t, J=8.8 Hz, 1H), 6.39 (s, 1H), 7.04 (m, 1H), 7.31 (m, 2H), 7.42 (m, 3H), 7.53 (m, 4H), 7.67 (m, 1H), 7.80 (m, 2H), 8.05 (m, 2H), 8.37 (s, 1H). $^{13}$C NMR (100 MHz, CDCl$_3$) δ4.8, 5.4, 5.9, 6.7, 6.8, 10.1, 14.6, 20.9, 21.2, 23.1, 26.5, 34.5, 37.2, 43.1, 46.7, 58.4, 70.3, 72.3, 74.9, 75.1, 76.5, 78.8, 79.2, 80.9, 84.3, 128.4, 128.6, 129.5, 130.2, 131.0, 133.3, 133.8, 136.1, 139.0, 140.6, 162.8, 166.9, 169.2, 169.9, 172.3, 201.9. IR (solid, cm$^{-1}$) 3570, 3085, 2956, 2877, 1728, 1645, 1454, 1371, 1240. LRMS (Electrospray), m/z 1066 (M+H)$^+$. HRMS (FAB) calculated for C$_{59}$H$_{80}$NO$_{13}$Si$_2$ (M+H)$^+$ 1066.5168, found 1066.5161.

The silica gel column was then flushed with MeOH, and yielded 2', 7-bis(triethylsilyl) Taxol primary amine (91 mg, 30%). This result would indicate that the imine product is somewhat unstable, and a portion was hydrolyzed during chromatography. $^1$H NMR (400 MHz, CDCl$_3$) δ0.50–0.66 (m, 2H), 0.87–0.99 (m, 18H), 1.11 (s, 3H), 1.17 (s, 3H), 1.64 (s, 3H), 1.74 (m, 1H), 1.88 (m, 2H), 1.90 (s, 3H), 2.15 (s, 3H), 2.29 (s, 3H), 2.49 (m, 1H), 3.71 (d, J=6.96 Hz, 1H), 4.12 (d, J=8.4 Hz, 1H), 4.26 (d J=8.4, 1H), 4.22 (br s, 1H), 4.28 (d, J=6.6 Hz, 1H), 4.42 (dd, J=6.6, 10.66 Hz, 1H), 4.90 (d, J=8.04 Hz, 1H), 5.60 (d, J=7.32 Hz, 1H), 6.00 (t, J=8.8 Hz, 1H), 6.40 (s, 1H), 7.13 (m, 1H), 7.31 (m, 4H), 7.51 (m, 2H), 7.64 (1H), 8.0 (m, 2H). LRMS (Electrospray), m/z 978 (M+H)$^+$. IR (solid, cm$^{-1}$) 3433, 956, 2914, 2877, 1726, 1495, 1369, 1265, 1107.

Example 2

This example demonstrates the conversion of 2',7-bis(triethylsilyl) Taxol to 2',7-bis(triethylsilyl) Taxol imine and further conversion to Taxol primary amine.

A sample of 2',7-bis(triethylsilyl) Taxol (130.8 mg, 0.12 mmQl) was dissolved in THF (1.2 mL). Zirconocene chloride hydride was added (93.6 mg, 0.36 mmol) and the reaction stirred at 25° C. under $N_2$. After 1.5 hours the reaction appeared complete by TLC analysis. The crude mixture was poured into cold hexanes, and the resulting precipitated Zr complexes were filtered off. The solvent was removed under reduced pressure, to give 128.6 mg of a white solid. The intermediate imine product was not isolated. The solids were reconstituted in a 1% w/w HCl/95% EtOH solution (4 Ml). After 3 days the reaction appeared complete by TLC analysis. The reaction mixture was diluted with water and washed with hexanes. The aqueous portion was then removed and neutralized to Ph 7 with saturated NaHCO$_3$ solution. The neutralized aqueous portion was then extracted with CH$_2$Cl$_2$. The resulting organic layer was separated, dried over MgS0$_4$, and concentrated to a solid. Silica gel chromatography (7% MeOH/CH$_2$Cl$_2$) yielded 44.6 mg Taxol primary amine (50% overall yield): mp 160°–162° C. $^1$H NMR (400 Mhz, CDCl3) δ1.11 (s, 3H), 1.22 (s, 3H), 1.64 (s, 3H), 1.81 (s, 3H), 1.97 (m, 3H), 2.21 (s, 3H), 2.22 (s, 3H), 2.52 (m, 1H), 3.70 (d, J=6.96 Hz, 1H), 4.12 (d, J=8.4 Hz, 1H), 4.26 (d, J=8.76, 1H), 4.28 (br s, 2H), 4.38 (dd, J=6.6, 10.8 Hz, 1H), 4.91 (d, J=7.68 Hz, 1H), 5.61 (d, J=6.96 Hz, 1H), 6.12 (t, J=8.4 Hz, 1H), 6.26 (s, 1H), 7.22 (m, 1H), 7.37 (m, 4H), 7.5 (m, 2H), 7.64 (m, 1H), 8.04 (m, 2H). $^{13}$C NMR (100 MHz, CDCl$^3$) δ9.6, 15.0, 20.9, 21.5, 22.5, 26.8, 35.3, 35.6, 43.2, 45.7, 58.5, 58.6, 71.2, 72.2, 74.9, 75.6, 75.7, 76.4, 79.2, 81.0, 84.5, 127.0, 128.3, 128.7, 128.9, 129.2, 130.2, 133.0, 133.8, 141.6, 142.5, 166.9, 170.2, 171.3, 173.1, 203.8. IR (solid, cm$^{-1}$) 3512, 2941, 2899, 1724, 1493, 1452, 1371, 1242, 1070. LRMS (Electrospray), m/z 750 (M+H)$^+$. HRMS (FAB) calcd for C$_{40}$H$_{48}$NO$_{13}$ (M+H)$^+$ 750.3126, found 750.3130.

Example 3

This example demonstrates the conversion of Taxol to 2',7-bis(triethylsilyl) Taxol with further conversion to 2',7-bis(triethylsilyl) Taxol imine and final conversion to Taxol primary amine. This method demonstrates the conversion of Taxol to primary amine without isolation of intermediates.

A sample of Taxol (14.7 g, 17 mmol) was dissolved in pyridine (150 mL) and chlorotriethylsilane (23.03 g, 147 mmol) was added. The reaction was stirred at 25° C. under $N_2$. After 20 hours the reaction appeared complete by TLC analysis (7% MeOH/CH$_2$Cl$_2$). The mixture was concentrated to remove the pyridine. The residue was dissolved in CH$_2$Cl$_2$ and washed with water, 10% CuSO$_4$, NaHCO$_3$ and brine successively. The organic layer was dried over MgSO$_4$, and concentrated to yield 20.89 g of the crude 2,7'-bis(triethylsilyl) Taxol.

A portion of crude 2',7-bis(triethylsilyl) Taxol (14.50 g, 13.4 mmol) was dissolved in dry THF (150 mL). Zirconocene chloride hydride (7.75 g, 30.2 mmol) was added. The reaction was stirred at 25° C. under $N_2$. After 20 hours the reaction appeared complete by TLC analysis. The mixture was poured into cold hexanes, and the resulting precipitated Zr complexes were filtered off. The solution was concentrated to yield 17 g of the crude 2,7'-bis(triethylsilyl) Taxol imine.

A portion of crude 2',7-bis(triethylsilyl) Taxol imine (8.36 g) was dissolved in 1% HCl/EtOH (180 mL) and the reaction was stirred at 25° C for 20 hours. The reaction appeared complete by TLC analysis. The mixture was poured into 800 mL of water and washed with hexane (180 mL×3). The aqueous layer was neutralized with NaHCO$_3$ to pH=7.0. The product was extracted with $CH_2Cl_2$. The organic layer was removed and concentrated to a solid. Silica gel chromatography (5% $MeOH/CH_2Cl_2$) yielded Taxol primary amine (2.41 g, 52% overall yield based on 5 g of Taxol used). The isolated material was spectroscopically identical to previously isolated samples.

Example 4

This example demonstrates the conversion of cephalomannine to 2',7-bis(triethylsilyl)cephalomannine A sample of cephalomannine (525.5 mg, 0.63 mmol) was dissolved in pyridine (6.3 mL). Chlorotriethylsilane (1.06 mL, 6.3 mmol) was added and the reaction stirred under $N_2$ at 25° C. After 2.75 days the reaction appeared complete by TLC analysis. The mixture was diluted with $CH_2Cl_2$, and washed with water, 10% $CuSO_4$, and brine successively. The organic layer was dried over $MgSO_4$, and concentrated to a solid. Silica gel chromatography (10–25% EtOAc/hexane) then yielded 2',7-bis(triethylsilyl)cephalomannine (569.9 mg, 85%). $^1H$ NMR (400 MHz, $CDCl_3$) $\delta$0.42 (m, 6H), 0.57 (m, 6H), 0.79 (m, 9H), 0.92 (m, 9H), 1.21 (s, 3H), 1.22 (s, 3H), 1.65 (s, 3H), 1.69 (s, 3H), 1.71 (s, 3H), 1.79 (s, 3H), 1.90 (m, 2H), 2.00 (s, 3H), 2.1 (m, 1H), 2.17 (s, 3H), 2.35 (m, 1H), 2.53 (s, 3H), 3.82 (d, J=6.96 Hz, 1H), 4.19 (d, J=8.0 Hz, 1H), 4.29 (d, J=8.04, 1H), 4.47 (dd, J=6.6, 10.62 Hz, 1H), 4.62 (d, J=2.16 Hz, 1H), 4.93 (d, J=8.04 Hz, 1H), 5.55 (d, J=7.32 Hz, 1H), 5.69 (d, J=7.32 Hz, 1H), 6.22 (t, J=8.8 Hz, 1H), 6.42 (m, 1H), 6.45 (s ,1H), 6.67 (d, J=8.8 Hz, 1H), 7.26 (m, 3H), 7.34, (m, 2H), 7.50 (m, 2H), 7.59 (m, 1H), 8.12 (m, 2H). $^{13}C$ NMR (100 MHz, CDCl3) $\delta$4.4, 5.4, 6.6, 6.8, 10.2, 12.4, 14.0, 14.2, 20.9, 21.6, 23.1, 26.6, 35.6, 37.3, 43.4, 46.7, 55.3, 58.5, 71.4, 72.2, 72.3, 74.9, 75.0, 75.1, 78.9, 81.2, 84.3, 126.5, 127.8, 128.5, 128.6, 128.8, 129.3, 130.3, 131.4, 131.7, 133.7, 138.8, 140.4, 167.1, 168.7, 169.3, 170.2, 171.7, 201.8. LRMS (Electrospray), m/z 1060 (M+H)$^+$. IR (solid, cm$^{-1}$) 3446, 2956, 2912, 2877, 1726, 1641, 1494, 1371, 1267, 1240, 1136, 1109.

Example 5

This example demonstrates the conversion of 2',7-bis (triethylsilyl)cephalomannine to 2',7-bis(triethylsilyl) cephalomannine imine.

A sample of 2',7-bis(triethylsilyl)cephalomannine (98.3 mg, 0.093 mmol) was dissolved in THF (1 mL). Zirconocene chloride hydride was added (119.6 mg, 0.464 mmol) and the reaction stirred at 25° C. under $N_2$. After 2 hours the reaction appeared complete by TLC analysis. The crude mixture was poured into cold hexanes, and the resulting precipitated Zr complexes were filtered off. The solvent was removed under reduced pressure, to give 96 mg of a white solid. Silica gel chromatography (20% EtOAc/hexane) then yielded 2,7-bis(triethylsilyl)cephalomannine imine (30 mg, 31%). $^1H$ NMR (400 MHz, $CDCl_3$) $\delta$0.55 (m, 12H), 0.93 (m, 18H), 1.10 (s, 3H), 1.14 (s, 3H), 1.45 (s, 3H), 1.63 (s, 3H), 1.68 (s, 3H), 1.85 (m, 3H), 1.89 (s, 3H), 2.14 (s, 3H), 2.30 (s, 3H), 2.46 (m, 1H), 3.66 (d, J=6.96 Hz, 1H), 4.17 (d, J=8.40 Hz, 1H), 4.22 (d, J=8.40 Hz, 1H), 4.30 (d, J=8.44, 1H), 4.41 (dd, J=6.6, 10.66 Hz, 1H), 4.49 (d, J=8.44 Hz, 1H), 4.90 (d (J=8.10 Hz, 1H), 5.56 (d, J=6.96 Hz, 1H), 5.86 (t, J=8.08 Hz, 1H), 5.99 (q, J=8.8 Hz, 1H), 6.38 (s, 1H), 7.02 (m, 1H), 7.29 (m, 2H), 7.44 (m, 2H), 7.55 (m, 2H), 7.67 (m, 1H), 7.88 (s, 1H), 8.05 (m, 2H). $^{13}C$ NMR (100 MHz, $CDCl_3$) $\delta$4.9, 5.3, 5.4, 6.7, 6.8, 10.1, 11.2, 14.4, 14.5, 20.9, 21.1, 23.0, 26.5, 34.7, 37.3, 43.0, 43.2, 46.8, 58.4, 70.2, 72.3, 74.9, 75.1, 76.5, 78.7, 78.9, 80.9, 84.3, 128.3, 128.4, 128.5, 130.2, 133.2, 133.8, 137.0, 137.4, 139.7, 140.7, 167.0, 167.1, 169.3, 169.9, 201.8. LRMS (Electrospray), m/z 1044 (M+H)$^+$. IR (solid, cm$^{31\ 1}$) 3527, 2956, 2914, 2877, 1728, 1454, 1371, 1267, 1240, 1109.

The silica gel column was then flushed with MeOH, and yielded 2',7-bis(triethylsilyl) Taxol primary amine (30 mg, 30%), chromatographically and spectroscopically identical to the second product isolated in Example 1.

Example 6

This example demonstrates the conversion of 2',7-bis (triethylsilyl)cephalomannine to 2',7-bis(triethylsilyl) cephalomannine and further conversion to Taxol primary amine.

A sample of 2',7-bis(triethylsilyl)cephalomannine (186.7 mg, 0.18 mmol) was dissolved in THF (1.8 mL). Zirconocene chloride hydride was added (227.2 mg, 0.88 mmol) and the reaction stirred at 25° C. under $N_2$. After 2.5 hours the reaction appeared complete by TLC analysis. The crude mixture was poured into cold hexanes, and the resulting precipitated Zr complexes were filtered off. The solvent was removed under reduced pressure, to give 235 mg of a white solid. The intermediate imine product was not isolated. The solids were reconstituted in EtOH (4 mL) and 3N HCl (0.3 mL). After 16 hours the reaction appeared complete by TLC analysis. The reaction mixture was diluted with water and washed with hexanes. The aqueous portion was then removed and neutralized to pH 7 with saturated $NaHCO_3$ solution. The neutralized aqueous portion was then extracted with $CH_2Cl_2$. The resulting organic layer was removed, dried over $MgSO_4$, and concentrated to a solid. Silica gel chromatography (7% $MeOH/CH_2Cl_2$) yielded Taxol primary amine (47.0 mg, 35% overall yield), chromatographically and spectroscopically identical to the product isolated in Example 2.

Example 7

This example demonstrates the conversion of 2',7-bis (triethylsilyl)oxidized Taxol B to 2',7-bis(triethylsilyl) oxidized Taxol B imine and further conversion to Taxol primary amine. This is an example of conversion of an oxidized Taxol B derivative to a primary amine.

A sample of 2',7-bis(triethylsilyl) Taxol B was treated with ozone in methanol to form the 2',7-bis(triethylsilyl)-pyruvamide-Taxol compound. A small sample (approximately 5 mg) of this compound was then dissolved in THF (approximately 0.050 mL) and a small amount of zirconocene chloride hydride was added (approximately 5 mg) The mixture was stirred overnight at rt and analyzed by TLC, and LRMS (Electrospray), m/z 978 (M+H). The TLC data ($SiO_2$, 25% EtOAc/hexane) shows no more starting material and a polar spot corresponding to a protected primary amine. The LRMS data shows a peak corresponding to the 2',7-bis(triethylsilyl) Taxol primary amine. The 2',7-bis(triethylsilyl)pyruvamide-Taxol imine is apparently not very stable and it degraded to the protected primary amine in the reaction mixture.

Example 8

This example demonstrates the conversion of Taxol C to 2',7-bis(triethylsilyl) Taxol C.

A sample of Taxol C (142 mg, 0.17 mmol) was dissolved in pyridine (2 ml) and chlorotriethylsilane (281 µl, 1.7 mmol) was added. The reaction was stirred at 25° C. under $N_2$. After 20 hours the reaction appeared almost complete by TLC analysis. The mixture was concentrated to remove the pyridine. The residue was dissolved in $CH_2Cl_2$ and washed with water, 10% $CuSO_4$, $NaHCO_3$ and brine successively. The organic layer was dried over $MgSO_4$, and concentrated to yield the crude product. Silica gel chromatography (3% $MeOH/CH_2Cl_2$) yielded 160 mg of 2,7'-bis(triethylsilyl) Taxol C (88.5% yield). $^1H$ NMR (400 MHz/$CDCl_3$):δ0.42 (m, 5H), 0.56 (m, 1H), 0.67 (m, 1H), 0.78 (m, 10H), 0.91 (m, 2H), 1.15 (s, 2H), 1.23 (m, 5H), 1.28 (s, 2H), 1.57 (m, 2H), 1.69 (s, 3H), 1.89 (m, 4H), 2.16 (m, 2H), 2.21 (s, 1H), 2.23 (s, 3H), 2.38 (m, 1H), 2.50 (s, 3H), 2.54 (m, 1H), 3.81 (d, J=6.96 Hz, 2H), 4.20 (d, J=8.4 Hz, 1H), 4.30 (d, J=8.4 Hz, 1H), 4.44 (m, 1H), 4.58 (m, 1H), 4.97 (m, 1H), 5.54 (m, 1H), 5.69 (d, J=6.96 Hz, 1H), 6.23 (m, 1H), 6.29 (s, 1H), 6.35 (d, J=11.2 Hz, 1H), 7.27 (m, 2H), 7.30 (m, 1H), 7.37 (m, 3H), 7.51 (m, 2H), 7.59 (m, 1H), 8.11 (d, J=7.32 Hz, 2H). $^{13}C$ NMR (100 MHz/$CDC_3$): δ4.4, 5.4, 6.6, 6.8, 9.7, 13.9, 14.9, 20.9, 22.4, 23.0, 25.4, 26.8, 31.4, 35.6, 35.8, 36.3, 43.3, 45.6, 55.1, 58.6, 71.5, 72.2, 74.9, 75.2, 75.6, 79.2, 81.2, 84.5, 126.5, 127.9, 128.7, 128.8, 130.3, 132.9, 133.7, 138.6, 142.7, 167.1, 170.2, 172.14, 171.6, 172.7, 203.8. LRMS (Electrospray), m/z 1077 $(M+H)^+$, 1099 $(M+Na)^+$.

Example 9

This example demonstrates the conversion of 2',7-bis(triethylsilyl) Taxol C to 2',7-bis(triethylsilyl) Taxol C imine and further conversion to 10-deacetyl Taxol primary amine. This is an example of conversion of a Taxol C derivative to a primary amine.

A sample of 2,7'-bis(triethylsilyl) Taxol C (46 mg, 0.043 mmol) was dissolved in dry THF (2 ml). Zirconocene chloride hydride (27 mg, 0.105 mmol) was added. The reaction was stirred at 25° C. under $N_2$. After 20 hours the reaction appeared complete by TLC analysis. The mixture was concentrated to yield 80 mg of the crude 2,7'-bis (triethylsilyl) Taxol C imine. LRMS (Electrospray), m/z 1063 (M+H).

A sample of crude 2,7'-bis(triethylsilyl) Taxol C imine (80 mg) was dissolved in 0.75% of HCl/95%EtOH (1.5 ml) and the reaction was stirred at 25° C. for 20 hours. The reaction appeared to go no further when analyzed by TLC, so, it was quenched by pouring into 20 ml of water and washing with hexane (40 ml×2). The aqueous layer was neutralized with $NaHCO_3$ to pH=7.0. The product was extracted with CH2C12. The organic layer was removed and concentrated to a solid. Silica gel chromatography (5% $MeOH/CH_2Cl_2$) yielded 14 mg of Taxol primary amine (44% overall yield). The product was chromatographically and spectroscopically identical to the product isolated in Example 2.

Example 10

This example demonstrates the conversion of 10-deacetyl-7-xylosyl Taxol C to per(triethylsilyl)-10-deacetyl-7-xylosyl Taxol C.

A sample of 10-deacetyl-7-xylosyl Taxol C (10-DAXTC, 536.5 mg, 0.57 mmol) was dissolved in pyridine (5.7 mL). Chlorotriethylsilane (1.92 mL, 11.4 mmol) was added and the reaction stirred under $N_2$ at 25° C. After 2.75 days the reaction appeared complete by TLC analysis. The mixture was diluted with $CH_2Cl_2$, and washed with water, 10% $CuSO_4$, and brine successively. The organic layer was dried over $MgSO_4$, and concentrated to a solid. Silica gel chromatography (20% EtOAc/hexane) yielded per(triethylsilyl)-10-DAXTC (617.5 mg, 86%). $^1H$ NMR (400 MHz, $CDCl_3$) δ0.41 (m, 7H), 0.65 (m, 21H), 0.98 (m, 32H), 1.12 (s, 3H), 1.22 (m, 5H), 1.25 (s, 3H), 1.54 (m, 2H), 1.75 (m, 1H), 1.80 (s, 3H), 1.91 (s, 3H), 1.99 (m, 1h), 2.15 (m, 1H), 2.21 (t, J=7.32 Hz, 2H), 2.35 (m, 1H), 2.47 (s, 3H), 2.81 (m, 1H), 3.31 (d, J=3.28 Hz, 1H), 3.44 (d, J=2.2 Hz, 1H), 3.54 (t, J=3.28 Hz, 1H), 3.91 (d, J=6.6 Hz, 1H), 3.99 (dd, J=2.20, 11.56 Hz, 1H), 4.13 (dd, J=6.96, 10.28 Hz, 1H), 4.20 (d, J=8.44 Hz, 1H), 4.27 (d, J=1.84 Hz, 1H), 4.28 (d, J=8.44 Hz, 1H), 4.41 (s, 1H), 4.58 (d, J=1.84 Hz, 1H), 4.92 (d, J=8.44 Hz, 1H), 5.13 (d, J=1.44 Hz, 1H), 5.51 (dd, J=1.80, 7.38 Hz, 1H), 5.66 (d, J=7.0 Hz, 1H), 6.24 (t, J=8.8 Hz, 1H), 6.38 (d, J=9.16 Hz, 1H), 7.30 (m, 3H), 7.37 (m, 2H), 7.50 (m, 2H), 7.59 (m, 1H), 8.10 (m, 2H). LRMS (Electrospray), m/z 1418 $(M+Na)^+$. IR (solid, $cm^{-1}$) 3440, 2954, 2912, 1875, 1755, 1731, 1604, 1493, 1457, 1271, 1244, 1109.

Example 11

This example demonstrates the conversion of per (triethylsilyl)-10-DAXTC to per(triethylsilyl)-10DAXTC imine, followed by further conversion to 10-deacetyl-7-xylosyl Taxol primary amine. This is an example of conversion of a 7-xylosyl Taxol derivative to a 7-xylosylTaxol primary amine.

A sample of per(triethylsilyl)-10-DAXTC (20.3 mg, 0.015 mmol) was dissolved in THF (0.15 mL). Zirconocene chloride hydride was added (22.5 mg, 0.087 mmol) and the reaction stirred at 25° C. under $N_2$. After 41 hours, the reaction appeared complete by TLC analysis. The crude mixture was poured into cold hexanes, and the resulting precipitated Zr complexes were filtered off. The solvent was removed under reduced pressure to give 17 mg of per (triethylsilyl)-10-DAXTC imine. LRMS (Electrospray), m/z 1380 (M+H). Additional characterization was not performed. The imine intermediate was reconstituted in $CH_3CN$ (1.6 mL), HF (0.237 mL), and pyridine (0.085 mL) at 0° C. The reaction slowly warmed to 25° C. After 20 hours the reaction appeared complete by TLC analysis. LRMS analysis at that point showed a strong peak that matched the expected m/z for 10-deacetyl-7-xylosyl Taxol primary amine. LRMS (Electrospray), m/z 840 $(M+H)^+$. Additional analysis was not performed.

Example 12

This example demonstrates the conversion of Taxol to 2',7-bis(trimethylsilyl) Taxol.

A sample of Taxol (512 mg, 0.6 mmol) was dissolved in pyridine (5 mL) and chlorotrimethylsilane (0.9 mL, distilled) was added. The reaction was stirred at 25° C. under $N_2$. After 20 hours the reaction appeared complete by TLC analysis. The mixture was concentrated to remove the pyridine. The residue was dissolved in $CH_2Cl_2$ and washed with water, 10% $CuSO_4$, $NaHCO_3$ and brine successively. The organic layer was dried over $MgSO_4$, and concentrated to yield 580 mg of the crude 2',7-bis(trimethylsilyl) Taxol. $^1H$ NMR (400 MHz, $CDCl_3$) δ0.064 (s, 9H), 0.088 (s, 9H), 1.86 (m, 1H), 1.94 (s, 3H), 2.17 (s, 3H), 2.21 (m, 1H), 2.44 (m, 2H), 2.55 (s, 3H), 3.83 (d, J=7.2 Hz, 1H), 4.19 (d, J =8.4 Hz, 1H), 4.30 (d, J=8.4 Hz, 1H), 4.40 (m, 1H), 4.61 (d, J=2.2 Hz, 2H), 4.93 (m, 1H), 5.70 (m, 2H), 6.25 (m, 1H), 6.40 (s, 1H), 7.12 (d, J=8.4 Hz, 1H), 7.35 (m, 6H), 7.49 (m, 3H), 7.59 (m, 1H), 7.75 (m, 2H), 8.11 (d, J=6.9 Hz, 2H). LRMS (Electrospray), m/z 998 $(M+H)^+$.

Example 13

This example demonstrates the conversion of 2',7-bis (trimethylsilyl) Taxol to 2',7-bis(trimethylsilyl) Taxol imine, followed by further conversion to Taxol primary amine. This is an example of the use of an alternative protecting group in the conversion of Taxol to Taxol primary amine.

A sample of crude 2',7'-bis(trimethylsilyl) Taxol (387 mg, 0.4 mmol) was dissolved in dry THF (5 mL). Zirconocene chloride hydride (164.8 mg, 1.04 mmol) was added. The reaction was stirred at 25° C. under $N_2$. After 20 hours the reaction appeared complete by TLC analysis. The mixture was concentrated to yield 557 mg of the crude 2',7-bis (trimethylsilyl) Taxol imine. No data was collected on this labile material.

The crude 2',7-bis(trimethylsilyl) Taxol imine (557 mg) was dissolved in 1% HCl/EtOH (15 mL) and the reaction was stirred at 25° C. for 20 hours. The reaction was complete by TLC analysis, so, the mixture was poured into 80 mL of water and washed with hexane (30 mL×3). The aqueous layer was neutralized with $NaHCO_3$ to pH=7.0. The product was extracted with $CH_2Cl_2$. The organic layer was concentrated to a solid. Silica gel chromatography (5% MeOH/$CH_2Cl_2$) yielded 132 mg of Taxol primary amine (41% overall yield), chromatographically and spectroscopically identical to a standard sample from Example 2.

Example 14

This example demonstrates the conversion of 2',7-bis (trichloroethoxycarbonyl) Taxol to 2',7-bis (trichloroethoxycarbonyl) Taxol imine, followed by further conversion to Taxol primary amine. This is an example of the use of an another protecting group in the conversion of Taxol to Taxol primary amine.

A sample of 2',7-bis(trichloroethoxycarbonyl) Taxol (21.9 mg, 0.018 mmol) was dissolved in THF (0.18 mL). Zirconocene chloride hydride was added (28.2 mg, 0.109 mmol) and the reaction stirred at 25° C. under $N_2$. After 23 hours, the reaction appeared complete by TLC analysis. The crude mixture was poured into cold hexanes, and the resulting precipitated Zr complexes were filtered off. The solvent was removed under reduced pressure, to give 11 mg of a light yellow solid. The mass spectral data was consistent with the 2',7-bis(TROC) Taxol imine structure. LRMS (Electrospray), m/z 1188 (M+H). Additional characterization was not performed. The imine intermediate was reconstituted in MeOH (0.096 mL) and AcOH (0.096 mL). Zinc dust was added (5.8 mg) and the reaction stirred at 25° C. After 24 hours LRMS analysis indicated Taxol primary amine as one of a mixture of products; LRMS (Electrospray), m/z 750 (M+H)$^+$. Additional analysis was not performed.

Example 15

This example demonstrates the conversion of Taxol primary amine to Taxol.

A sample of Taxol primary amine (95.1 mg, 0.127 mmol) was dissolved in pyridine (12.7 mL). Benzoyl chloride was added (0.0147 mL, 0.127 mmol) and the reaction proceeded at 25° C. under $N_2$. After 2 hours TLC analysis indicated the reaction was complete. The crude mixture was diluted with EtOAc, and washed with water, 10% $CuSO_4$, and brine successively. The organic layer was removed and concentrated to a solid. Silica gel chromatography (5% MeOH/$CH_2Cl_2$) then yielded 80.6 mg of Taxol (74%), spectroscopically identical to a natural sample. 1H NMR (400 MHz, $CDCl_3$) δ1.12 (s, 3H), 1.21 (s, 3H), 1.66 (s, 3H), 1.77 (s, 3H), 1.85 (m, 1H), 2.20 (s, 3H), 2.29 (m, 2H), 2.36 (s, 3H), 2.50 (m, 1H), 3.77 (dd, J=1.0, 6.96 Hz, 1H), 4.19 (d, J=8.44 Hz, 1H), 4.30 (d, J=8.4 Hz, 1H), 4.37 (dd, J=6.60, 10.62 Hz, 1H), 4.77 (d J=2.92 Hz, 1H), 4.92 (dd, J=2.16, 9.84 Hz, 1H), 5.65 (d, J=6.96 Hz, 1H), 5.76 (dd, J=2.56, 8.8 Hz, 1H), 6.19 (t, J=8.8 Hz, 1H), 6.26 (s, 1H), 7.13 (d, J=8.8 Hz, 1H), 7.36 (m, 5H), 7.45 (m, 5H), 7.71 (m, 2H), 8.1 (m, 2H). $^{13}$C NMR (100 MHz, $CDCl_3$) δ9.7, 14.9, 20.9, 21.9, 22.7, 26.9, 35.7, 35.8, 43.3, 45.8, 55.2, 58.6, 72.2, 72.3, 73.3, 75.1, 75.7, 76.6, 79.0, 81.2, 84.5, 127.1, 127.2, 128.4, 128.7, 128.8, 129.0, 129.3, 130.3, 132.0, 133.2, 133.6, 133.7, 138.1, 142.0, 167.0, 167.3, 170.5, 171.3, 172.8, 203.7. LRMS (Electrospray), m/z 854 (M+H)$^+$. IR (solid, cm$^{-1}$) 3498, 3435, 2941, 2899, 1724, 1664, 1516, 1485, 1452, 1371, 1268, 1242, 1070.

Example 16

This example demonstrates the conversion of Taxol primary amine to Taxol (Schotten-Baumann conditions).

A sample of Taxol primary amine (7.5 mg, 0.01 mmol) was dissolved in EtOAc (1 mL) and saturated $NaHCO_3$ solution (1 mL). Benzoyl chloride was added (0.0011 mL, 0.01 mmol) and the reaction proceeded at 25° C. After 6 days the reaction was diluted with EtOAc, and washed with water and brine successively. The organic layer was then concentrated to a solid. $^1$H NMR analysis of the resulting residue was identical to that obtained in Example 15, indicating Taxol as the only product. No additional analysis was performed.

Example 17

This example demonstrates the conversion of 10-deacetyl Taxol to 2',7-bis(triethylsilyl)-10-deacetyl Taxol.

A sample of 10-deacetyl Taxol (335.0 mg, <0.41 mmol, purity <90%) was dissolved in pyridine (8.0 mL). Chlorotriethylsilane (1.06 mL, 6.3 mmol) was added and the reaction stirred under $N_2$ at 25° C. After 14 hours the reaction appeared complete by TLC analysis. The mixture was diluted with $CH_2Cl_2$, and washed with water, 10% $CuSO_4$, and brine successively. The organic layer was dried over $MgSO_4$, and concentrated to a solid. Silica gel chromatography (30% EtOAc/hexane) yielded 293.5 mg of 2',7-bis(triethylsilyl)-10-deacetyl Taxol (68%). $^1$H NMR (400 MHz, CDCl3) δ8.12 (d, J=7.3 Hz, 2H), 7.75 (d, J=7.3 Hz, 2H), 7.61–7.29 (m, 13H), 7.12 (d, J=8.8 Hz, 1H, NH), 6.30 (t, J=8.4 Hz, 1H, H-13), 5.70–5.65. (m, 2H), 5.15 (d, J=1.8 Hz, 1H, H-10), 4.90 (d, J=7.7 Hz, 1H, H-5), 4.68 (d, J=2.2 Hz, 1H, H-2'), 4.39 (dd, J=6.6, 10.6 Hz, 1H, H-7), 4.32 (d, J=8.4 Hz, 1H, H-20a), 4.27 (d, 1.8H, OH-10), 4.22 (d, J=8.1 Hz, 1H, H-20b), 3.88 (d, J=6.6 Hz, 1H, H-3), 2.54 (s, 3H, OAc-4), 2.50–2.33 (m, 2H), 2.12–2.06 (m, 1H), 1.93 (s, 3H, Me-18), 1.75 (s, 3H, Me-19), 1.21 (s, 3H, Me-16), 1.09 (s, 3H, Me-17), 1.01–0.77 (m, 18H, H-TES), 0.60–0.37 (m, 12H, H-TES); LRMS (Electrospray) m/e 1040 (M+H)+, 1057 (M+NH$_4$)$^+$.

Example 18

This example demonstrates the conversion of 2',7-bis (triethylsilyl)-10-deacetyl Taxol to 2',7-bis(triethylsilyl)-10-deacetyl Taxol imine.

A sample of 2',7-bis(triethylsilyl)-10-deacetyl Taxol (96.4 mg, 0.096 mmol) was dissolved in THF (1.1 mL). Zirconocene-chloride hydride was added (74.4 mg, 0.29 mmol) and the reaction stirred at 25° C. under $N_2$. After 3.5 hours the reaction appeared complete by TLC analysis. The crude mixture was poured into cold hexanes, and the resulting precipitated Zr complexes were filtered through a bed of celite. The solvent was removed under reduced pressure, to give crude 2',7-bis(triethylsilyl)-10-deacetyl Taxol imine. Chromatography ($SiO_2$, 5% MeOH/$CH_2Cl_2$) followed by another attempt ($SiO_2$, 30% EtOAc/hexane) yielded 68 mg of a slightly yellow compound that appeared slightly contaminated by $^1$H NMR. Additional characterization using NMR data shows the distinct imine proton signal at 8.37 ppm, as well as other distinct signals (see data below). The mass spectral data shows a strong molecular ion for the desired imine. The spectral data strongly suggests the 2',7-bis(triethylsilyl)-10-deacetyl Taxol imine structure. The impurities are difficult to remove and may result from decomposition of the imine on silica gel. We have seen previously that the 2',7-bis(triethylsilyl) Taxol imine decomposes to the 2',7-bis(triethylsilyl) Taxol primary on silica gel (see Example 1). $^1$H NMR (400 MHz, CDCl$_3$) δ 8.37 (s, 1H, imine-H), 8.05 (d, J=7.0 Hz, 2H), 7.82–7.29 (m, 12H), 7.05 (t, J=7.3 Hz, 1H), 5.94 (t, J=9.2 Hz, 1H, H-13), 5.54 (d, J=7.3 Hz, 1H, H-2), 5.04 (d, J=1.8 Hz, 1H, H-10), 4.90 (d, J=7.7 Hz, 1H, H-5), 4.59 (d, J=8.4 Hz, 1H), 4.51 (d, J=8.4 Hz, 1H), 4.34 (dd, J=3.8, 6.9 Hz, 1H, H-7),4.25 (d, J=8.8 Hz, 1H,), 4.19 (d, J=1.8 Hz, 1H, OH-10), 4.13 (d, J=8.8 Hz, 1H,), 3.73 (d, J=7.0 Hz, 1H, H-3), 2.44 (m, 1H, H-6a), 2.32 (s, 3H, OAc-4), 1.89 (m, 1H), 1.81 (s, 3H, Me-18), 1.69 (s, 3H, Me-19), 1.64 (m, 1H), 1.14 (s, 3H, Me-16), 1.04 (s, 3H, Me-17), 0.95–0.87 (m, 18H, TES-H), 0.60–0.49 (m, 12H, TES-H); LRMS (Electrospray) m/e 1024 (M+H)$^+$.

Example 19

This example demonstrates the conversion of 2',7-bis(triethylsilyl)-10-deacetyl Taxol to 2',7-bis(triethylsilyl)-10-deacetyl Taxol imine, followed by further conversion to 10-deacetyl Taxol primary amine. This is an example of conversion of a 10-deacetyl Taxol derivative to 10-deacetyl Taxol primary amine.

A sample of 2',7-bis(triethylsilyl)-10-deacetyl Taxol (203.5 mg, 0.19 mmol) was dissolved in THF (2.1 mL). Zirconocene chloride hydride was added (149 mg, 0.58 mmol) and the reaction stirred at 25° C. under N$_2$. After 10 hours, the reaction appeared complete by TLC analysis. The crude mixture was poured into cold hexanes, and the resulting precipitated Zr complexes were filtered off. The solvent was removed under reduced pressure, to give a white solid. The intermediate imine product was not isolated. The solids were reconstituted in a 1% w/w concentrated HCl/95% EtOH solution (6 mL). After 14 hours the reaction was appeared complete by TLC analysis. The reaction mixture was diluted with water and washed with hexanes. The aqueous portion was then removed and neutralized to pH 7 with saturated NaHCO$_3$ solution. The neutralized aqueous portion was then extracted with CH$_2$Cl$_2$. The resulting organic layer was removed, dried over MgSO$_4$, and concentrated to a solid. Silica gel chromatography (7% MeOH/CH$_2$Cl$_2$) yielded 59.0 mg of 10-deacetyl Taxol primary amine (43% overall yield). $^1$H NMR (400 MHz, CDC$_3$) δ8.05 (d, J=7.7 Hz, 2H), 7.64 (t, J=7.2 Hz, 1H), 7.51 (m, 2H), 7.38 (m, 5H), 6.13 (t, J=9.0 Hz, 1H, H-13), 5.64 (d, J=7.0 Hz, 1H, H-2), 5.19 (s, 1H, H-10), 4.92 (d, J=8.1 Hz, 1H, H-5), 4.32–4.27 (m, 4H), 4.22 (dd, J=6.8, 10.8 Hz, 1H, H-7), 4.15 (d, J=7.7 Hz, 1H, H-20b), 3.87 (d, J=7.3 Hz, 1H, H-3), 2.58 (m, 1H, 1H-6a), 2.24 (s, 3H, OAc-4), 2.02 (t, J=9.3 Hz, 2H, H-14), 1.90 (s, 3H, Me-18), 1.82 (m, 1H, H-6b), 1.73 (s, 3H, Me-19), 1.21 (s, 3H, Me-16), 1.10 (s, 3H, Me-17). $^{13}$C NMR (100 MHZ, DMSO) δ10.37, 14.30, 21.38, 22.89, 27.10, 35.85, 37.03, 39.46, 39.68, 39.88, 40.09, 40.30, 40.51, 40.71, 43.46, 46.51, 57.53, 59.23, 70.15, 71.35, 74.33, 75.31, 77.07, 77.42, 80.84, 84.28, 127.64, 127.64, 127.81, 127.81, 128.41, 128.59, 129.24, 130.08, 130.60, 133.97, 136.62, 137.23, 142.53, 165.76, 170.22, 173.81, 209.92. LRMS (ElectrospraY) m/e 708.3 (M+H)$^+$. IR (solid, cm$^{-1}$) 3448, 3064, 2939, 2898, 1724, 1602, 1452, 1438, 1270, 1245.

Example 20

This example demonstrates the conversion of 10-deacetyl Taxol C to 2',7-bis(triethylsilyl)-10-deacetyl Taxol C.

A sample of 10-deacetyl Taxol C (58.2 mg, <0.072 mmol, purity <80%, $^1$H NMR (400 MHz, CDCL$_3$) δ 8.10 (d, J=7.3 Hz, 2H), 7.61–7.38 (m, 8H), 6.25 (d, J=8.8 Hz, 1H, NH), 6.19 (t, J=9.0 Hz, 1H, H-13), 5.68 (d, J=7.3 Hz, 1H, H-3'), 5.57 (dd, J=2.6, 9.8 Hz, 1H, H-2), 5.18 (s, 1H, H-10), 4.92 (d, J=7.7 Hz, 1H, H-5), 4.67 (s, 1H, H-2'), 4.31–4.19 (m, 4H), 3.89 (d, J=7 Hz, 1H, H-3), 2.34 (s, 3H, OAc-4), 2.28 (m, 1H, H-6a), 2.19 (t, J=7.7 Hz, 1H), 1.83 (m, 1H), 1.81 (s, 3H, Me-18), 1.75 (s, 3H, Me-19), 1.24 (s, 3H, Me-16), 1.13 (s, 3H, Me-17); LRMS (Electrospray) m/e 806.3 (M+H)$^+$) was dissolved in pyridine (1.8 mL). Chlorotriethylsilane (0.250 mL, 1.44 mmol) was added and the reaction was stirred under N$_2$ at 25° C. After 14 hours, the reaction appeared complete by TLC analysis. The mixture was diluted with CH$_2$Cl$_2$, and washed with water, 10% CuSO$_4$, and brine, successively. The organic layer was dried over anhydrous MgSO$_4$, and concentrated to a solid. Silica gel chromatography (20% EtOAc/hexane) yielded 2',7-bis(triethylsilyl)-10-deacetyl Taxol C (24.0 mg). This material was carried on to the conversion in Example 21 without further characterization.

Example 21

This example demonstrates the conversion of 2',7-bis(triethylsilyl)-10-deacetyl Taxol C to 2',7-bis(triethylsilyl)-10-deacetyl Taxol C imine and further conversion to 10-deacetyl Taxol primary amine.

A sample of 2',7-bis(triethylsilyl)-10-deacetyl Taxol C (24.0 mg, 0.023 mmol) was dissolved in THF (0.26 mL). Zirconocene chloride hydride was added (24.2 mg, 0.093 mmol) and the reaction stirred at 25° C. under N$_2$. After 14 hours the reaction appeared complete by TLC analysis. The crude mixture was poured into cold hexanes, and the resulting precipitated Zr complexes were filtered off. The solvent was removed under reduced pressure, to give a white solid. The intermediate imine product was not isolated. The solids were reconstituted in EtOH (1 mL) and 3N HCl (0.3 mL). After 3 days the reaction appeared complete by TLC analysis. The reaction mixture was diluted with water and washed with hexanes. The aqueous portion was then removed and neutralized to pH 7 with saturated NaHCO$_3$ solution. The neutralized aqueous portion was then extracted with CH$_2$Cl$_2$. The resulting organic layer was removed, dried over MgSO$_4$, and concentrated to a solid. Silica gel chromatography (10% MeOH/CH$_2$Cl$_2$) yielded 10-deacetyltaxol primary amine (3.0 mg, 18% overall yield). The product was chromatographically and spectroscopically identical to the standard made in Example 19.

Example 22

This example demonstrates the conversion of 10-deacetyl Taxol primary amine to docetaxel (TAXOTERE). This effectively demonstrates the conversion of 10-deacetyl Taxol to docetaxel.

A sample of 10-deacetyltaxol primary amine (64.4 mg, 0.091 mmol) was dissolved in ethyl acetate (9.1 mL) and a saturated solution of NaHCO$_3$ (9.1 mL) was added. To this biphasic mixture was added di-tert-butyl dicarbonate (0.042 mL, 0.18 mmol). The mixture was stirred for 14 hours at 25° C. TLC analysis (7% MeOH/CH$_2$Cl$_2$) showed the reaction was finished, so it was diluted with ethyl acetate, washed with water and brine and the organic phase was dried over MgSO$_4$. After concentrating, the residue was purified by chromatography (SiO$_2$, 5% MeOH/CH$_2$Cl$_2$) to give 54.8 mg of docetaxel (74.5% yield). The $^1$H NMR, $^{13}$C NMR and mass spectral data for the isolated compound matched with reported data for docetaxel.

Example 23

This example demonstrates the conversion of Taxol to primary amine using no protecting groups.

A sample of Taxol (1.018 g, 1.192 mmol) was dissolved in THF (11.9 mL), and zirconocene chloride hydride was added in small portions over 10 minutes. The mixture was stirred for 2 days at 25° C. The mixture was analyzed by TLC (7% MeOH/CH$_2$Cl$_2$) and it appeared that very little if any Taxol remained, so it was concentrated to a yellow/brown solid. The solid was dissolved in ethanol (95%, 126 mL) and concentrated HCl was added (0.83 mL). The yellow/brown solution was stirred for 14 hours at 25° C. A white precipitate had formed during the acidic hydrolysis. TLC analysis of the reaction mixture indicated that a substantial amount of Taxol primary amine was formed. The mixture was worked up by filtering out the white precipitate. The filtrate was partitioned between methylene chloride (200 mL, containing organic impurities) and 10% HCl (200 mL, containing the Taxol primary amine hydrochloride salt). The phases were separated. Each phase was back extracted with fresh portions of the other solution (2×50 mL each). The combined acidic aqueous phases were neutralized with NaHCO$_3$ (saturated solution) and extracted with methylene chloride (2×100 mL). The methylene chloride phase was then washed with brine (1×50 mL), dried over anhydrous MgSO$_4$, and concentrated to a light yellow solid (167 mg). The $^1$H NMR data shows that the light yellow solid is very clean Taxol primary amine (18% yield).

The combined initial organic phases containing organic impurities were washed with NaHCO$_3$ (saturated solution), brine, dried over anhydrous MgSO$_4$, and concentrated to a yellow solid (478 mg). The yellow solid was analyzed by $^1$H NMR and it contains several unidentified compounds, plus little unreacted Taxol.

Example 24

This example demonstrates the conversion of a mixture of purified Taxol A and purified Taxol B (cephalomannine) to Taxol primary amine.

To 100 mg of a mixture of Taxol A and cephalomannine (50 mg of each) was added zirconocene chloride hydride (94 mg, 0.36 mmol), followed by 0.8 ml of THF (0.15 M). The reaction was stirred under argon for four days at 25° C. The reaction was concentrated to a solid. The solids were reconstituted in a 1% w/w concentrated HCl/95% EtOH solution (3 mL). The mixture was stirred overnight at 25° C. The reaction was worked up by pouring into water. The pH was adjusted to 4 by addition of 3N HCl. The aqueous solution was extracted with CH$_2$Cl$_2$ (2×50 mL). The aqueous layer was neutralized to pH 7 by addition of NaHCO$_3$(saturated solution), followed by extraction with CH$_2$Cl$_2$. The organic layer containing the primary amine was dried over MgSO$_4$, concentrated to a solid and the product was analyzed by LRMS, which matched the expected m/z for the primary amine. LRMS (Electrospray), m/z 750 (M+H)$^+$.

Example 25

This example demonstrates the conversion of a mixture of impure Taxol A, impure Taxol B (cephalomannine) and impure Taxol C to Taxol primary amine.

To 50 mg of a mixture of Taxol A and cephalomannine (Taxol B) and Taxol C (55% by assay of the three—Taxol (A+B+C)) in 2 mL of THF was added zirconocene chloride hydride (77 mg, 0.30 mmol). The reaction was stirred under argon for six days at 25° C. Analysis by TLC indicated that the reaction was not finished so a large excess of zirconocene chloride hydride was added, followed by 0.5 mL of THF. After stirring overnight, the reaction was concentrated to a solid. The solids were reconstituted in a 1% w/w concentrated HCl/95% EtOH solution (10 mL). The mixture was stirred overnight at 25° C. The reaction was worked up by pouring into water. The pH was adjusted to 4 by addition of 3N HCl. The aqueous solution was extracted with CH$_2$Cl$_2$ (2×50 mL). The aqueous layer was neutralized to pH 7 by addition of NaHCO$_3$ (saturated solution), followed by extraction with CH$_2$Cl$_2$. The organic layer containing the primary amine was dried over MgSO$_4$ and concentrated to a solid (65 mg). The analytical data shows that the isolated product is impure, however, both $^1$H NMR and MS data agree well with a standard sample of Taxol primary amine.

Example 26

This example demonstrates the conversion of Taxol primary amine to Taxol primary amine salts.

A sample of Taxol primary amine (100 mg, 0.13 mmol) was dissolved in CH$_2$Cl$_2$ (10 mL) and HCl (15 mM in Et$_2$O; 10 ml, 150 mmol) was added. The reaction was stirred at 25° C. for 2 minutes. The mixture was concentrated to remove the solvents. The residue was redissolved in CH$_2$Cl$_2$ and precipitated in hexane. Filtration yielded 85 mg of Taxol PA•HCl (83%). mp 165° C.

A sample of Taxol PA•HCl (50 mg, 0.064 mmol) was dissolved in 0.5 ml of water. It was neutralized to pH 7.0 by addition of saturated NaHCO$_3$, followed by extraction with CH$_2$Cl$_2$. The organic layer was concentrated and chromatographed (3% MeOH/CH$_2$Cl$_2$ was used as mobile phase) to yield 30 mg of Taxol primary amine (63% yield). The $^1$H NMR and LRMS data agree well with a standard sample of Taxol primary amine.

Example 27

This example illustrates one preferred method for deacetylation of Taxol. 500 mg (0.57 mmol) of Taxol in 10 ml of THF were introduced into a 25 ml round bottomed flask equipped with a magnetic stir bar. 10 ml of 30% H$_2$O was added followed by 960.0 mg of NaHCO$_3$ and the mixture was then stirred at room temperature overnight. The mixture was then extracted with methylene chloride/water (50:50 by volume). The organic phase was collected and dried over anhydrous magnesium sulfate. The solvent was then evaporated under reduced pressure to obtain a crude product, that was subsequently purified. 457.2 mg of pure 10-deacetyl Taxol were recovered resulting in a 96% yield. NMR data and mass spec. match known samples.

The description and examples set forth herein are intended to illustrate representative embodiments of the invention. The claims which follow are not intended to be limited to the specific disclosed embodiments. The invention is susceptible to modification, variation and change without departing from the proper scope or fair meaning of the following claims.

We claim:
1. A compound useful for the production of Taxol or precursors thereof comprising:

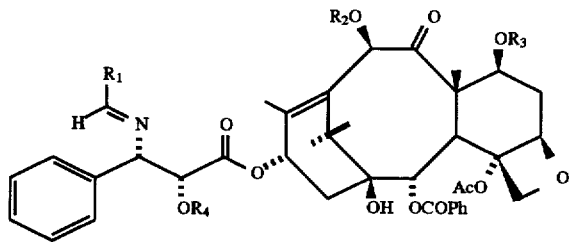

wherein,
$R_1$ =alkyl, aryl, carbonyl or ether group;
$R_2$ =H, alkyl, aryl, ester, ether or protecting group;
$R_3$ =H, alkyl, aryl, ether, ester, glycoside, or protecting group;
$R_4$ =H or protecting group.

2. The compound of claim 1 wherein:
$R_1$=alkyl or aryl group;
$R_2$=H, Ac or a protecting group;
$R_3$=H, xylosyl, or protecting group; and
$R_4$=H or a protecting group.

3. The compound of claim 2, wherein $R_1$ is $C_6H_5CO$,

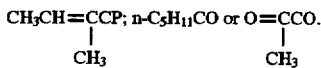

4. The compound of claim 3, wherein $R_1$ is $C_6H_5CO$.
5. The compound of claim 3, wherein $R_1$ is

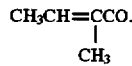

6. The compound of claim 3, wherein $R_1$ is n-$C_5H_{11}CO$.
7. The compound of claim 3, wherein $R_2$ is Ac, $R_3$ is H, and $R_4$ is H.
8. The compound of claim 3, wherein $R_2$ is H, $R_3$ is H, and $R_4$ is H.
9. The compound of claim 3, wherein $R_2$ is Ac, $R_3$ is xylosyl, and $R_4$ is H.
10. The compound of claim 3, wherein $R_2$ is H, $R_3$ is xylosyl, and $R_4$ is H.
11. The compound of claim 3, wherein $R_2$, $R_3$ and $R_4$ is a protecting group selected from the group consisting of triethylsilyl, trimethylsilyl, and trichloroethoxycarbonyl.
12. The compound of claim 3, wherein $R_3$ and $R_4$ is a protecting group selected from the group consisting of triethylsilyl, trimethylsilyl, and trichloroethoxycarbonyl.
13. The compound of claim 3, wherein $R_3$ and $R_4$ is triethylsilyl.
14. The compound of claim 3, wherein $R_4$ is a protecting group selected from the group consisting of triethylsilyl, trimethylsilyl, and trichloroethoxycarbonyl.
15. The compound of claim 3, wherein $R_4$ is triethyisilyl.
16. A compound useful for the production of Taxol or precursors thereof comprising:

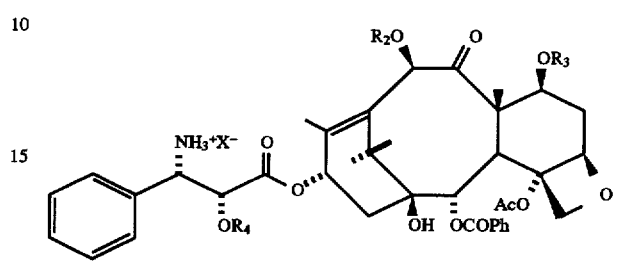

wherein,
$R_2$ =H, Ac or a protecting group;
$R_3$ =H, xylosyl or protecting group;
$R_4$ =H or protecting group; and
X=deprotonated organic acid.

17. The compound of claim 16, wherein X is $OOCCF_3$.
18. The compound of claim 16, wherein X is $O_3SC_6H_4CH_3$.
19. The compound of claim 16, wherein $R_2$ is Ac and $R_3$ is H.
20. The compound of claim 16, wherein $R_2$ is H and $R_3$ is H.
21. The compound of claim 16, wherein $R_2$ is Ac and $R_3$ is xylosyl.
22. The compound of claim 16, wherein $R_2$ is H and $R_3$ xylosyl.
23. The compound of claim 16, wherein $R_2$, $R_3$ and $R_4$ is the protecting group selected from the group consisting of triethylsilyl, trimethylsilyl, and trichloroethoxycarbonyl.
24. The compound of claim 16, wherein $R_3$ and $R_4$ is a protecting group selected from the group consisting of triethylsilyl, trimethylsilyl, and trichloroethoxycarbonyl.
25. The compound of claim 16, wherein $R_3$ and $R_4$ is triethylsilyl.
26. The compound of claim 16, wherein $R_4$ is a protecting group selected from the group consisting of triethylsilyl, trimethylsilyl, and trichloroethoxycarbonyl.
27. The compound of claim 16, wherein $R_4$ is triethylsilyl.

* * * * *

UNITED STATES PATENT AND TRADEMARK OFFICE
CERTIFICATE OF CORRECTION

| | | |
|---|---|---|
| PATENT NO. | : 5,679,807 | |
| APPLICATION NO. | : 08/380679 | |
| DATED | : October 21, 1997 | |
| INVENTOR(S) | : Christopher K. Murray et al. | |

It is certified that error appears in the above-identified patent and that said Letters Patent is hereby corrected as shown below:

In claim 3, column 21, lines 26-31, delete chemical drawings:
"$C_6H_5CO$, $$CH_3CH=C(CH_3)CP;\ n\text{-}C_5H_{11}CO\ or\ O=C(CH_3)CO.$$

"

and insert -- phenyl, $CH_3CH=C(CH_3)-$, $n-C_5H_{11}-$, or $CH_3C(O)-$ -- therefor.

In claim 4, column 21, line 32, delete "$C_6H_5CO$" and insert -- phenyl -- therefor.

In claim 5, column 21, lines 34-38, delete chemical drawing:
" $CH_3CH=C(CH_3)CO.$ "

and insert -- $CH_3CH=C(CH_3)-$ -- therefor.

Signed and Sealed this
Twenty-fifth Day of October, 2011

David J. Kappos
*Director of the United States Patent and Trademark Office*